United States Patent [19]

Turner et al.

[11] Patent Number: 5,250,690
[45] Date of Patent: Oct. 5, 1993

[54] HALOALKOXY ANILIDE DERIVATIVES OF 2-4(-HETEROCYCLIC OXYPHENOXY)ALKANOIC OR ALKENOIC ACIDS AND THEIR USE AS HERBICIDES

[75] Inventors: James A. Turner, Pittsburg; Wendy S. Jacks, Walnut Creek, both of Calif.; Paul S. Zorner, Durham, N.C.; Susan K. Moore, Pittsburg, Calif.

[73] Assignee: DowElanco, Indianapolis, Ind.

[21] Appl. No.: 722,580

[22] Filed: Jun. 27, 1991

Related U.S. Application Data

[63] Continuation of Ser. No. 439,063, Nov. 20, 1989, abandoned, which is a continuation-in-part of Ser. No. 730,353, May 2, 1985, abandoned.

[51] Int. Cl.$^5$ ............... C07D 241/40; C07D 239/34; C07D 213/643; C07D 263/58
[52] U.S. Cl. .................. 544/354; 544/316; 546/157; 546/291; 548/171; 548/217
[58] Field of Search ............ 546/291, 302, 157; 71/94; 544/316, 354; 548/217, 171; 504/235, 242, 244, 267, 270

[56] References Cited

U.S. PATENT DOCUMENTS

| | | | |
|---|---|---|---|
| 4,447,259 | 5/1984 | Ohyama et al. | 71/94 |
| 4,586,950 | 5/1986 | Pasteris | 71/92 |
| 4,737,184 | 4/1988 | Pasteris | 71/90 |
| 4,741,765 | 5/1988 | Pasteris et al. | 71/93 |
| 4,750,930 | 6/1988 | Shapiro | 71/90 |
| 4,752,322 | 6/1988 | Dumas | 71/90 |
| 4,795,483 | 1/1989 | Gates | 71/90 |
| 4,818,273 | 4/1989 | Kleschick et al. | 71/90 |
| 5,032,168 | 7/1991 | Turner | 71/92 |
| 5,034,050 | 7/1991 | Turner et al. | 504/267 |
| 5,180,417 | 1/1993 | Turner | 504/246 |

OTHER PUBLICATIONS

Egli et al., Chem. Abstracts, vol. 96(25), abst. No. 96:212,542k, Jun. 21, 1982.
Japanese J54122-728 (Derwent Publications, 79972B/44).
Great Britain 2051-778 (Derwent Publications, 04338D/04).

*Primary Examiner*—Alan L. Rotman
*Attorney, Agent, or Firm*—S. Preston Jones

[57] ABSTRACT

The present invention is directed to novel substituted aniline compounds, the optically active isomers of said compounds, compositions containing said compounds, and the use of these compounds in the selective kill and control of grassy weeds in the presence of valuable crop plants, especially corn plants.

49 Claims, No Drawings

HALOALKOXY ANILIDE DERIVATIVES OF 2-4(-HETEROCYCLIC OXYPHENOXY)ALKANOIC OR ALKENOIC ACIDS AND THEIR USE AS HERBICIDES

CROSS-REFERENCE TO RELATED APPLICATION

This is a continuation of application Ser. No. 439,063 filed Nov. 20, 1989 (abandoned), which is a continuation-in-part of Ser. No. 06/730,353 filed May 2, 1985 (abandoned).

SUMMARY OF THE INVENTION

The present invention is directed to novel substituted aniline compounds, the optically active isomers of said compounds, compositions containing said compounds, and the use of these compounds in the selective kill and control of grassy weeds in the presence of valuable crop plants.

The active compounds of the present invention correspond to the formula

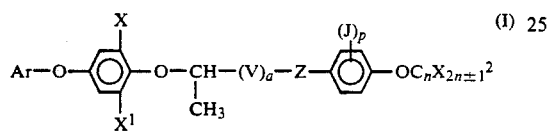

wherein
Ar represents

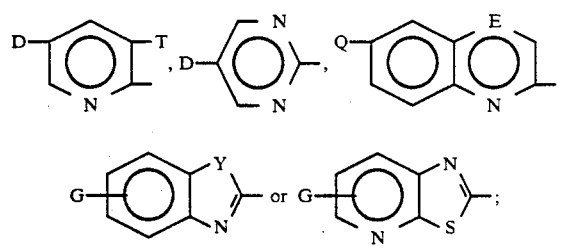

X and $X^1$ each independently represents —H or —F; each $X^2$ independently represents —H, —Br, —Cl or —F, with the proviso that at least one $X^2$ is other than —H and that all $X^2$'s cannot be —Br or —Cl;
Y represents oxygen or sulfur;
Z represents

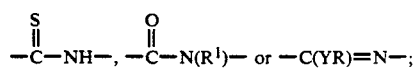

D represents —Br, —Cl, —I or —CF$_3$;
E represents =CH or =N;
G represents at the 5 or 6-ring position, —Br, —Cl, —F or —CF$_3$;
R represents $C_1$-$C_4$ alkyl;
$R^1$ represents —H, $C_1$-$C_4$ alkyl, —CH$_2$OH or the agriculturally acceptable salts (—COO$^\ominus$M$^{(+)}$);
J represents —Br, —Cl, —F, —I, —NO, —R, —CN, —OR, —NH$_2$, —NHR, —N(R)$_2$ or —COOR;
T represents —H, —Br, —Cl or —F;
Q represents —Br, —Cl, —F, or —CF$_3$;
V represents —CH$_2$CH$_2$— or —CH=CH—;
a represents an integer of 0 or 1;
n represents an integer of from 1 to 4, inclusive; and
p represents an integer of 0, 1 or 2.

The compounds of Formula I most preferred are those compounds wherein a is 0, n represents an integer of from 1 to 3, p is 0 and Z represents

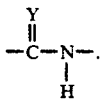

The term "$C_1$-$C_4$ alkyl" as employed in the present specification and claims designates alkyl groups which can be straight or branched chain containing from 1 to 4 carbon atoms or cycloalkyl of 3 or 4 carbon atoms.

In the present invention, it is to be noted that all substituent groups are sterically compatible with each other. The term "sterically compatible" is employed to designate substituent groups which are not affected by steric hindrance as defined in "The Condensed Chemical Dictionary", 7th edition, Reinhold Publishing Co., N.Y., page 893 (1966) which definition is as follows:

"steric hindrance. A characteristic of molecular structure in which the molecules have a spatial arrangement of their atoms such that a given reaction with another molecule is prevented or retarded in rate."

Steric hindrance may be further defined as compounds having substituents whose physical bulk does not require confinement within volumes insufficient for the exercise of their normal behavior as discussed in "Organic Chemistry" of D. J. Cram and G. Hammon, 2nd edition, McGraw-Hill Book Company, N.Y., page 215 (1964).

The compounds of the present invention contain the optically active center

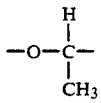

and can exist in optically active stereoisomeric forms such as the R and S enantiomeric forms. The various mixtures and racemates of the above isomers are within the scope of the present invention. Additionally, the R enantiomer of such compounds have been found to be more active biologically than the S enantiomer and may be prepared and used whenever the greater activity justifies the extra expenses of preparing the more active isomer.

A general discussion of the isomer activity difference phenomenon can be found in A. Albert, Selective Toxicity, 4th ed., Met Luen & Co., Ltd., London, 1968, pp. 387-390 and more particeular discussions in A. Fredga and B. Åberg, "Stereoisomerism in plant growth regulators of the auxin type", Ann. Rev. Plant Physiology 16:53-72, 1965 and in E. J. Lien, J. F. R. DeMiranda and E. J. Airens, "Quantitative structure-activity correlation of optica isomers", Molecular Pharmacology 12:598-604, 1976.

The compounds produced by the process of the present invention are generally solid materials having low mammalian toxicity. The compounds are substantially insoluble in water and moderately soluble in common organic solvents.

The compounds of the present invention, hereinafter referred to as "active compounds" or "active ingredients", have been found to be active as herbicides for the pre- and postemergent kill and control of undesirable vegetation, for example, grassy or graminaceous weeds and especially for the postemergent control of these weeds in the presence of crop plants including corn, soybeans, wheat, sugar beets, rice and cotton.

The present invention encompasses herbicidal compositions containing one or more of these active ingredients as well as methods of controlling said undesired weed plant growth, especially in the presence of said crop plants and especially in postemergent operations. Such methods comprise applying a herbicidally effective amount of one or more of said active ingredients to the locus of the undesired plants, i.e., the above-ground portions of the plants.

The term "herbicide" is used herein to mean an active ingredient which controls or adversely modifies the growth of plants because of phytotoxic or other effects substantial enough to seriously retard the growth of the plant or further to damage the plant sufficiently to kill the plant.

The terms "growth controlling" or "herbicidally effective" amount are employed to designate an amount of active ingredient which causes a modifying effect and includes deviations from natural development, killing, regulation, dessication, retardation, and the like.

The term "plants" means established vegetation.

The terms "control" or "controlling" as it relates to plant growth has the same meaning as employed hereinabove for the term "herbicide".

Representative compounds of the present invention are set forth below in Tables 1, 2, 3, 4 and 5.

TABLE 1

$$\text{D}-\underset{\text{N}}{\overset{\text{T}}{\bigcirc}}-\text{O}-\underset{\text{X}^1}{\overset{\text{X}}{\bigcirc}}-\text{O}-\underset{\text{CH}_3}{\text{CH}}-(\text{V})_a-\text{Z}-\underset{(J)_p}{\bigcirc}-\text{OC}_n\text{X}_{2n\pm1}{}^2 \qquad (\text{II})$$

| D | T | X | X$^1$ | (V)$_a$ | Z | OC$_n$X$_{2n\pm1}{}^2$ | J$_p$ |
|---|---|---|---|---|---|---|---|
| —Br | —Cl | —H | —F | — | —C(S)NH— | —OCF$_3$ | -2-NH$_2$ |
| —CF$_3$ | —Cl | —H | —H | — | —C(O)NH— | —OCF$_3$ | —H |
| —CF$_3$ | —F | —H | —H | — | —C(O)NH— | —OCF$_3$ | —H |
| —Br | —F | —H | —H | — | —C(O)NH— | —OCF$_3$ | —H |
| —I | —F | —F | —F | — | —C(O)NH— | —OCF$_3$ | -3-Cl |
| —CF$_3$ | —F | —F | —H | — | —C(OCH$_3$):N— | —OC$_2$F$_5$ | —H |
| —I | —Cl | —F | —F | — | —C(SCH$_3$):N— | —OCF$_2$CF$_2$H | —H |
| —CF$_3$ | —Br | —H | —H | — | —C(O)N(CH$_3$)— | —OCFHCF:CF$_2$ | -2-OCH$_3$ |
| —CF$_3$ | —H | —F | —H | — | —C(O)NH— | —OCF$_3$ | —H |
| —Cl | —Cl | —H | —H | — | —C(O)N(C$_4$H$_9$)— | —OCF$_3$ | —H |
| —CF$_3$ | —Cl | —F | —F | — | —C(O)NH— | —OCH$_2$CH(CH$_3$)CF$_3$ | -3-NO$_2$ |
| —CF$_3$ | —Cl | —H | —H | — | —C(O)NH— | —OCF$_2$CF$_2$H | -3,5-Cl$_2$ |
| —CF$_3$ | —Cl | —H | —H | — | —C(O)NH— | —OCF$_2$CF$_2$H | —H |
| —Cl | —F | —H | —H | — | —C(O)NH— | —OCF$_3$ | —H |
| —Cl | —Cl | —H | —H | —CH$_2$CH$_2$— | —C(O)NH— | —OCF$_3$ | —H |
| —CF$_3$ | —Cl | —H | —H | —CH:CH— | —C(O)NH— | —OCFClCFClH | —H |
| —Br | —F | —H | —H | — | —C(OC$_4$H$_9$):N— | —OCH$_2$CH:CHCl | —H |
| —I | —F | —F | —H | — | —C(O)NH— | —OCH$_2$F | —H |
| —CF$_3$ | —F | —H | —H | — | —C(O)NH— | —OCF$_2$CF$_2$H | -2-OCH$_3$ |
| —Cl | —F | —H | —H | — | —C(O)NH— | —OCF$_2$CF$_2$H | -3-Cl |

TABLE 2

$$\text{D}-\underset{\underset{\text{N}}{\text{N}}}{\bigcirc}-\text{O}-\underset{\text{X}^1}{\overset{\text{X}}{\bigcirc}}-\text{O}-\underset{\text{CH}_3}{\text{CH}}-(\text{V})_a-\text{Z}-\underset{(J)_p}{\bigcirc}-\text{OC}_n\text{X}_{2n\pm1}{}^2 \qquad (\text{III})$$

| D | X | X$^1$ | (V)$_a$ | Z | OC$_n$X$_{2n\pm1}{}^2$ | J$_p$ |
|---|---|---|---|---|---|---|
| —CF$_3$ | —H | —H | —CH:CH— | —C(O)NH— | —OCHF$_2$ | -3-NH$_2$ |
| —I | —H | —H | — | —C(O)NH— | —OCF$_3$ | —H |
| —Cl | —H | —H | — | —C(S)NH— | —OCF$_2$CF$_2$H | -3-Cl |
| —I | —F | —F | — | —C(S)NH— | —OCF$_2$CF(CF$_3$)$_2$ | -2-F |
| —Br | —H | —H | — | —C(O)N(CH$_3$)— | —OCF$_2$CHBrF | —H |
| —CF$_3$ | —F | —F | — | —C(O)N(CH$_3$)— | —OCF$_3$ | —H |
| —CF$_3$ | —H | —H | — | —C(O)NH— | —OCF$_2$CHBrF | —H |
| —CF$_3$ | —H | —H | — | —C(O)NH— | —OCF$_2$Br | -3-Cl |
| —Cl | —H | —H | — | —C(O)NH— | —OCF$_3$ | -3,5-Cl$_2$ |
| —Cl | —F | —F | — | —C(O)NH— | —OCF$_3$ | -2-NO$_2$ |
| —I | —H | —H | —CH$_2$CH$_2$— | —C(O)NH— | —OCF$_2$CHClF | —H |
| —Br | —F | —F | — | —C(S)NH— | —OCF$_2$CHFCF$_3$ | -2,3-F$_2$ |
| —Br | —H | —H | — | —C(O)NH— | —OCH$_2$CF$_3$ | -3-C$_2$H$_5$ |
| —Cl | —F | —H | — | —C(OCH$_3$):N— | —OCF$_3$ | —H |

TABLE 2-continued (III)

| D | X | X¹ | (V)$_a$ | Z | OC$_n$X$_{2n\pm1}^2$ | J$_p$ |
|---|---|----|---------|---|---------------------|-------|
| —I | —H | —H | — | —C(O)NH— | —OCF$_3$ | —H |

TABLE 3

(IV)

| E | Q | X | X¹ | (V)$_a$ | Z | OC$_n$X$_{2n\pm1}^2$ | J$_p'$ |
|---|---|---|----|---------|---|---------------------|--------|
| ≡CH | —F | —H | —H | — | —C(O)NH— | —OCF$_3$ | —H |
| ≡N | —Cl | —H | —H | — | —C(O)NH— | —OCF:CFH | —H |
| ≡N | —CF$_3$ | —F | —H | —CH$_2$CH$_2$— | —C(O)NH— | —OCF$_2$CF$_2$H | —H |
| ≡N | —Cl | —F | —H | — | —C(S)NH— | —OCF$_3$ | —H |
| ≡CH | —Br | —H | —H | —CH:CH— | —C(OCH$_3$):N— | —OCF$_2$CHBr$_2$ | -3-Br |
| ≡N | —Br | —F | —F | — | —C(SCH$_3$):N— | —OCF$_3$ | —H |
| ≡N | —F | —H | —H | — | —C(O)NH— | —OCF$_2$CF$_2$H | —H |
| ≡N | —Cl | —H | —H | — | —C(O)N(CH$_2$OH)— | —OC$_3$F$_7$ | -2-COOCH$_3$ |
| ≡N | —Cl | —H | —H | — | —C(O)NH— | —OCF$_2$CF$_2$Br | —H |
| ≡N | —F | —H | —H | — | —C(O)N(COONa)— | —OCHFCF$_3$ | -3-NO$_2$ |
| ≡N | —Cl | —H | —H | — | —C(O)NH— | —OCH$_2$CF$_2$CF$_2$H | —H |
| ≡N | —Cl | —H | —H | — | —C(O)NH— | —OCF$_2$CFBrH | —H |
| ≡N | —Cl | —H | —H | — | —C(O)NH— | —OCH$_2$(CF$_2$)$_2$CF$_3$ | —H |
| ≡N | —Cl | —H | —H | — | —C(O)NH— | —OCF$_3$ | —H |
| ≡CH | —Cl | —H | —H | — | —C(O)NH— | —OCF$_3$ | —H |
| ≡N | —Cl | —H | —H | — | —C(O)NH— | —OCH$_2$CH$_2$F | —H |
| ≡N | —Cl | —H | —H | — | —C(O)NH— | —OCF$_2$CF$_2$H | -2-CH$_3$ |
| ≡N | —Cl | —H | —H | — | —C(O)NH— | —OCH$_2$CF$_2$CF$_3$ | —H |
| ≡N | —Br | —H | —H | — | —C(O)NH— | —OCF$_3$ | —H |
| ≡N | —Br | —H | —H | — | —C(O)NH— | —OCF$_2$CF$_2$H | —H |
| ≡N | —F | —H | —H | — | —C(S)NH— | —OCF$_3$ | —H |
| ≡N | —Cl | —H | —H | — | —C(S)NH— | —OCH$_2$CF$_3$ | —H |
| ≡N | —Cl | —H | —H | — | —C(O)NH— | —OCF$_2$CCl$_3$ | —H |
| ≡N | —F | —H | —H | — | —C(O)N(C$_2$H$_5$)— | —OCF$_3$ | —H |
| ≡CH | —CF$_3$ | —H | —H | — | —C(O)NH— | —OCF$_2$CF:CF$_2$ | -2-CH$_3$ |
| ≡N | —Cl | —H | —H | — | —C(O)NH— | —CH$_2$CH:CHCl | —H |
| ≡N | —Cl | —H | —H | — | —C(O)NH— | —OCF$_2$CFHCF$_3$ | —H |
| ≡N | —F | —H | —H | — | —C(O)NH— | —OCF$_3$ | —H |
| ≡N | —Cl | —H | —H | — | —C(O)NH— | —OCF$_2$CF$_2$H | —H |
| ≡CH | —Cl | —F | —F | — | —C(O)NH— | —OCF$_2$CF$_2$H | -3-COOCH$_3$ |
| ≡CH | —Cl | —H | —F | — | —C(O)NH— | —OCClF$_2$ | -2-NH$_2$— |
| ≡N | —CF$_3$ | —H | —H | — | —C(S)NH— | —OCCl$_2$F | -3-I |
| ≡N | —F | —F | —F | — | —C(OCH$_3$):N— | —OCF$_3$ | -3-C$_4$H$_9$ |
| ≡N | —F | —H | —H | — | —C(O)NH— | —OCH(CH$_3$)CF$_3$ | —H |
| ≡N | —Cl | —H | —H | — | —C(O)NH— | —OCH$_2$CH$_2$CH$_2$F | —H |
| ≡N | —Cl | —H | —H | — | —C(O)NH— | —OCH$_2$CF$_3$ | -3-F |
| ≡N | —Cl | —H | —H | — | —C(O)NH— | —OCH(CH$_3$)C$_2$F$_5$ | —H |
| ≡N | —Cl | —H | —H | — | —C(O)NH— | —OCH(CH$_2$F)$_2$ | —H |
| ≡N | —Cl | —H | —H | — | —C(O)NH— | —OCF$_2$CCl$_2$H | —H |
| ≡N | —Cl | —H | —H | — | —C(O)NH— | —OCF$_2$CFClH | —H |
| ≡N | —Cl | —H | —H | — | —C(O)NH— | —OCH$_2$CF$_3$ | —H |
| ≡N | —Cl | —H | —H | — | —C(O)NH— | —OCF:CFCl | —H |
| ≡N | —F | —H | —H | — | —C(O)NH— | —OCH$_2$CF$_3$ | —H |
| ≡N | —Cl | —H | —H | — | —C(O)NH— | —OCF$_2$CBr$_2$H | —H |
| ≡N | —Cl | —H | —H | — | —C(O)NH— | —OCF$_2$CH$_2$Cl | —H |

TABLE 4

Structure (V): Benzoxazole-G-Y-N with O-phenyl(X,X¹)-O-CH(CH₃)-(V)ₐ-Z-phenyl(J)ₚ-OCₙX²₂ₙ±₁

| G | Y | X | X¹ | (V)ₐ | Z | OCₙX²₂ₙ±₁ | Jₚ |
|---|---|---|---|---|---|---|---|
| -6-CF₃ | S | —F | —F | — | —C(O)NH— | —OCF₂CH₃ | -2,3'-F₂ |
| -5-CF₃ | O | —H | —H | —CH₂CH₂— | —C(O)NH— | —OCF₂CF₂H | -3-I |
| -5-Br | S | —H | —H | —CH:CH— | —C(S)NH— | —OCHFCH₃ | -3-F |
| -6-Cl | S | —H | —H | — | —C(S)NH— | —OCF₂CF₂H | -3-CH₃ |
| -5-Br | O | —H | —H | — | —C(O)NH— | —OCF₂CF₂H | —H |
| -6-Br | S | —F | —H | — | —C(O)NH— | —OCFHCF:CF₂ | -2-Cl |
| -6-Cl | O | —H | —H | — | —C(O)NH— | —OCF₂CHBrF | —H |
| -5-F | O | —H | —H | — | —C(O)NH— | —OCH₂CF₃ | —H |
| -5-CF₃ | O | —H | —H | — | —C(O)NH— | —OCF₃ | —H |
| -5-CF₃ | O | —F | —F | — | —C(S)NH— | —OCFHCF:CF₂ | -2-CN |
| -6-Cl | O | —H | —H | — | —C(O)NH— | —OCH₂CH₂CF₃ | —H |
| -6-Cl | S | —H | —H | — | —C(OCH₃):N— | —OCF₃ | —H |
| -6-F | S | —H | —H | — | —C(O)NH— | —OCF₂Br | —H |
| -6-Cl | O | —F | —H | — | —C(O)NH— | —OCFClCH₂Cl | -2,3-(CH₃)₂ |
| -6-F | S | —H | —H | — | —C(O)NH— | —OCF₂H | -3-COOCH₃ |
| -6-Br | O | —H | —H | — | —C(O)NH— | —OCH(CF₃)CH₂Cl | —H |
| -6-F | O | —H | —H | — | —C(S)NH— | —CF₂CHBr₂ | —H |
| -6-Cl | O | —H | —H | — | —C(O)NH— | —OCF₃ | -2-NHCH₃ |

TABLE 5

Structure (VI): Pyrido-thiazole-G-N,S with O-phenyl(X,X¹)-O-CH(CH₃)-(V)ₐ-Z-phenyl(J)ₚ-OCₙX²₂ₙ±₁

| G | X | X¹ | (V)ₐ | Z | OCₙX²₂ₙ±₁ | Jₚ |
|---|---|---|---|---|---|---|
| -6-CF₃ | —H | —H | — | —C(O)NH— | —OCF₃ | —H |
| -6-F | —H | —H | — | —C(O)NH— | —OCHFCH₂Cl | —H |
| -5-CF₃ | —F | —F | — | —C(O)NH— | —OCF₃ | —H |
| -5-Cl | —H | —H | — | —C(O)NH— | —OCFClCH₂Cl | -3-F |
| -5-Br | —F | —H | — | —C(S)NH— | —OCF₃ | —H |
| -5-Br | —F | —F | — | —C(O)NH— | —OCF₃ | -2-Br |
| -6-Br | —H | —H | — | —C(O)NH— | —OCF₃ | —H |
| -6-Cl | —H | —H | — | —C(O)NH— | —OCF₂Cl | -3-OCH₃ |
| -6-Cl | —H | —H | — | —C(O)N(CH₃)— | —OCFHCF:CF₂ | —H |
| -6-Cl | —H | —H | — | —C(O)N(CH₃)— | —OCF₃ | —H |
| -5-CF₃ | —F | —H | — | —C(S)NH— | —OCF₃ | —H |
| -5-CF₃ | —F | —F | — | —C(OCH₃):N— | —OCF₂CF₂H | —H |
| -6-Br | —H | —H | —CH:CH— | —C(O)NH— | —OCF₃ | —H |
| -5-F | —F | —F | — | —C(O)NH— | —OCF₂CH₂Cl | —H |

The compounds of the present invention can be prepared employing procedures or procedures analogous to those taught in U.S. Pat. No. 4,270,948; British Patents 1,531,385; 1,563,850; 1,572,125 and 1,599,121; British Patent Application 2,123,819A; Japan Kokai 77,125,626 and European Patent Application 0023785 and 0044497 for preparing known amide compounds which are similar in structure to the compounds of the present invention. The preparative teachings of these above cited patents are incorporated herein by reference.

The compounds of the present invention which correspond to the formula

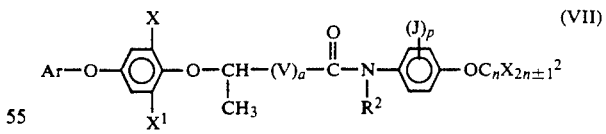

(VII)

can be prepared by reacting substantially equimolar amounts of an appropriate acid halide corresponding to the formula

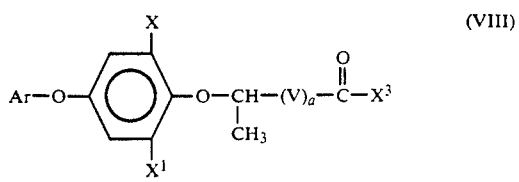

(VIII)

with an aniline corresponding to the formula

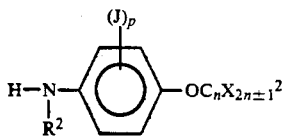

in the presence of an inert solvent and a hydrogen halide absorber (acid scavenger) in the above formulae, Ar, X, $X^1$, V, $X^2$, J, a, n and p are as hereinbefore defined, $X^3$ represents —Br, —Cl or —F and $R^2$ represents —H or $C_1$-$C_4$ alkyl.

The reaction is generally conducted at temperatures of from about 0° C. up to the reflux temperature of the mixture. Normally temperatures of from about 0° to about 100° C. are all that's necessary.

While not normally necessary, a catalyst can be employed, if desired. Representative catalysts include, for example, 4-dimethylaminopyridine and 1,4-diazabicyclo-2,2,2-octane.

Representative inert solvents for this reaction include, for example, chlorinated hydrocarbons (for example, methylene chloride), ether, toluene, pyridine, hexane, acetonitrile and the like.

Representative hydrogen halide absorbers include tertiary amines, alkali metal hydroxides and alkali metal carbonates. Alternatively, it has also been found that the addition of a molar excess of the amine reactant can function as the hydrogen halide absorber. Additionally, when pyridine is employed as the solvent, it can also function as the hydrogen halide absorber.

In an alternative procedure, these compounds can be prepared by the reaction of substantially equimolar amounts of an appropriate Ar compound corresponding to the formula

wherein Ar is as hereinbefore defined and $X^4$ represents —Br, —Cl, —F or —$SO_2R$ and an appropriate amide corresponding to the formula

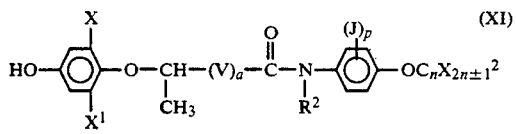

wherein $R^2$, Z, X, $X^1$, $X^2$, $(V)_a$, J, n and p are as hereinbefore defined. In carrying out this reaction, the reactants and a strong base such as an anhydrous alkali metal hydride, alkoxide, hydroxide or carbonate are mixed together in a dipolar, aprotic solvent such as, for example, dimethylformamide (DMF), acetone, methyl ethyl ketone, acetonitrile, dimethylsulfoxide (DMSO), sulfolane, N-methylpyrrolidone or the like. The reaction is advantageously carried out at elevated temperatures of from about 50° to 120° C.

In another procedure, these compounds can be prepared by the reaction of substantially equimolar amounts of an appropriate acid corresponding to the formula

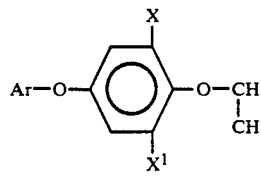

wherein Ar, X, $X^1$ and $(V)_a$ are as hereinbefore defined with an aniline corresponding to Formula IX in the presence of an inert reaction medium or solvent and a dehydrating agent such as, for example, dicyclohexylcarbodiimide (DCC) or a mixture of triphenyl phosphine and carbon tetrachloride. The reaction is usually conducted at temperatures of from about 0° C. to about 100° C. Other acceptable dehydrating agents and examples of their use in preparing amides from carboxylic acids and amines are included in Chapter 6, section 77 of the "Compendium of Organic Synthetic Methods", a 5 volume set, John Wiley & Sons; Wiley-Interscience Division, N.Y., N.Y. The above-indicated preparative teachings are incorporated herein by reference.

In another procedure, these compounds can be prepared by the reaction of substantially equimolar amounts of an appropriate acid ester corresponding to the formula

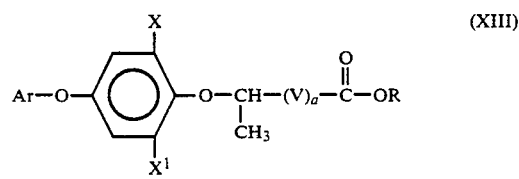

wherein Ar, R, X, $X^1$ and $(V)_a$ are as hereinbefore defined, with an aniline corresponding to Formula IX. This reaction is usually conducted in the presence of a polar solvent and at elevated temperatures of from about 50° C. to about 150° C. Depending on the specific reactants employed, a catalyst can be employed, if desired. Representative catalysts include those conventionally employed for ester-amide interchange.

The specific reaction times employed in the hereinabove and hereinafter set forth preparative procedures vary considerably and are dependent upon factors such as the solvent, base, catalyst, if employed, reaction temperature and the reactivity of the specific reactants employed. The reactions are for the most part complete in a period of from about 30 minutes to about 12 hours or more.

The compounds of the present invention which correspond to the formula

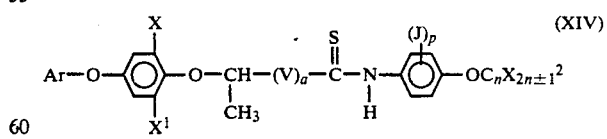

wherein Ar, X, $X^1$, $X^2$, V, J, a, n and p are as hereinbefore defined can be prepared directly from the corresponding acid amide of Formula VII employing conventional sulfurization procedures. Such procedures can be found in Wagner et al., "Synthetic Organic Chemistry", pages 827–831 (1953), John Wiley & Sons, N.Y., N.Y.. In a procedure taught in J. Org. Chem. 46, pages 3558-9 (1981) the acid amide of Formula VII wherein $R^2$ is hydrogen, is reacted with a sulfurization reactant such as phosphorous pentasulfide at a temperature of between about 0° and about 50° C.

The compounds of the present invention which correspond to the formula

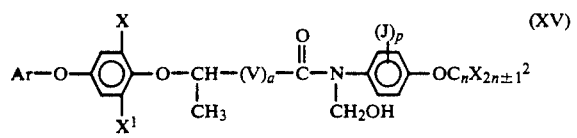

wherein Ar, X, $X^1$, $X^2$, V, J, a, n and p are as hereinbefore defined can be prepared by the reaction of the amide of Formula VII with formaldehyde or aqueous formaldehyde or paraformaldehyde in the presence of catalytic amounts of an acid or base. This reaction is well-known and conventional conditions for this reaction are employed. In one procedure, the compound of Formula VII wherein $R^2$ is hydrogen, an excess of formaldehyde, as an aqueous solution, and a catalytic amount of sodium hydroxide are mixed at a temperature of about room temperature up to the reflux temperature. The desired product is recovered therefrom.

The compounds of the present invention which correspond to the formula

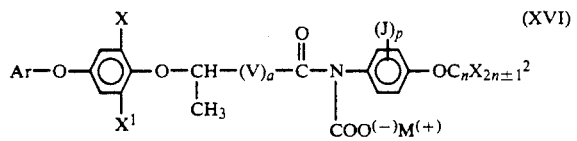

wherein Ar, X, $X^1$, $X^2$, V, J, a, n and p are as hereinbefore defined and —COO$^{(-)}$M$^{(+)}$ represents agriculturally acceptable salts, can be prepared from the amide of Formula VII wherein $R^2$ is hydrogen, by the reaction thereof, at a temperature of from about room temperature up to the reflux temperature, in a solvent such as THF, or the like, with a strong base such as an anhydrous alkali metal carbonate, hydroxide or hydride to first deprotonate the amide reactant. This reactant is thereafter reacted with an alkyl haloformate under conventional ester formation conditions.

The metal salts can easily be prepared by hydrolysis of the ester with stoichiometric amounts of a base, i.e., HO-M wherein M is one of Li, Na, K, Mg, Ba, Ca or N($R^2$)$_4$. This reaction is well known to those skilled in the art.

The compounds of the present invention which correspond to the formula

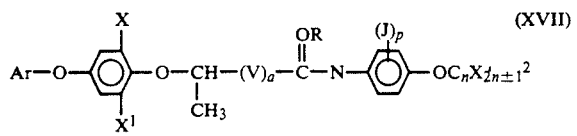

wherein Ar, X, $X^1$, $X^2$, V, R, J, a, n and p are as hereinbefore defined can be prepared employing the reaction procedure set forth in Chapter 9 of "The Chemistry of Amidines and Imidates", S. Patai, editor, John Wiley & Sons, N.Y., N.Y. (1975), by the reaction of the acid amide of Formula VII wherein $R^1$ is hydrogen with dialkylsulfate or trialkyloxonium fluoroborate followed by neutralization of the acid salt with a base.

The compounds of the present invention which correspond to the formula

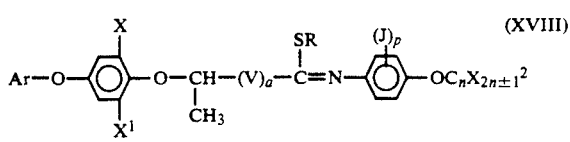

wherein Ar, X, $X^1$, $X^2$, V, R, J, a, n and p are as hereinbefore defined can be prepared from the reaction of the thio amide of Formula XIV and a non-nucleophilic base and excess alkyl halide. Representative bases include $K_2CO_3$ and NaH. Representative alkyl halides include the $C_1$-$C_4$ alkyl bromides, chlorides and iodides. The reaction is conducted in the presence of an inert solvent such, for example, acetone, DMF, DMSO, tetrahydrofuran (THF) or the like. The reaction is advantageously carried out at temperatures up to the boiling point of the solvent.

The desired product can be separated from the reaction product of the above preparative procedures employing conventional separatory procedures known to those skilled in the art including steps of solvent extraction, filtration, water washing, column chromatography, neutralization, acidification, crystallization and distillation.

The preparation of the optical isomer forms of the compounds of the present invention follow conventional procedures employed to prepare related compounds. Such procedures include those taught in U.S. Pat. application Ser. No. 30,274 (filed Jul. 14, 1983), European Patent Application 2800, 3890 and 6608; German OLS 29 49 728 and U.K. Patent Application GB 2042503A. The teachings of these applications are incorporated herein by reference thereto.

Since the hereinabove an hereinafter set forth compound preparation procedures employ only standard chemistry practices and it is known that slightly different reactants can require slightly different reaction parameters from those for other reactants, it is to be understood that minor modifications to the reaction parameters set forth such as the use of an excess of one reactant, the use of a catalyst, the use of high temperature and/or pressure equipment, high speed mixing and other such conventional changes are within the scope of this invention.

The following examples illustrate the present invention and the manner in which it can be practiced but as such, are not to be construed as limitations upon the overall scope of the same.

EXAMPLE I 2-(4-((3-Chloro-5-(trifluoromethyl)-2-pyridinyl)oxy)-phenoxy)-N-(4-(trifluoromethoxy)phenyl)propanamide

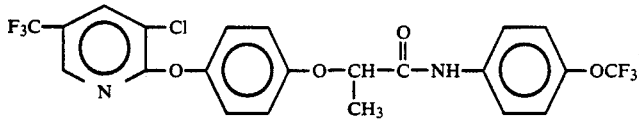

A solution of 5 millimoles (mmol) of 2-(4-((3-chloro-5-(trifluoromethyl)-2-pyridinyl)oxy)phenoxy)propionyl pionyl chloride (prepared using substantially the procedure of Step A of Example IV on 1.81 g (5 mmol) of the corresponding acid) in 10 ml of methylene chloride was added dropwise to an ice-cooled solution of 1.17 g (5.5 mmol) of 4-(trifluoromethoxy)aniline hydrochloride and 1.11 g (11 mmol) of triethylamine in 40 ml of methylene chloride. The reaction mixture was allowed to stir at room temperature for 2.5 hours and then poured into a dilute aqueous HCl solution. The organic layer was separated, washed with a saturated aqueous NaHCO3 solution, dried over MgSO4 and evaporated to dryness. The residual solid was recrystallized from methanol to give 1.61 g (62 percent of theoretical) of the above-named product as colorless crystals which melted at 140°–141° C. The structure of the product was confirmed by its IR and NMR spectrum. (Compound 1)

|  | % C | % H | % N |
|---|---|---|---|
| Analysis: | | | |
| Calc. for $C_{22}H_{15}ClF_6N_2O_4$: | 50.72 | 2.91 | 5.38 |
| Found: | 50.57 | 2.81 | 5.52 |

EXAMPLE II 2-(4-((3-Chloro-5-(trifluoromethyl)-2-pyridinyl)oxy)-phenoxy)-N-(3,5-dichloro-4-(1,1,2,2-tetrafluoroethoxy)-phenyl)propanamide

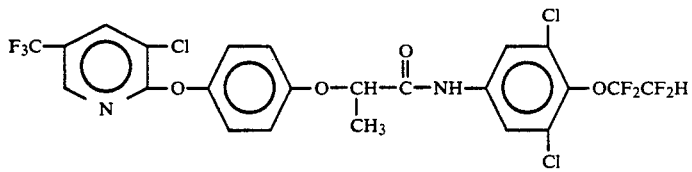

A solution of 3.5 mmol of 2-(4-((3-chloro-5-(trifluoromethyl)-2-pyridinyl)oxy)phenoxy)propionyl chloride in 15 ml of methylene chloride was added dropwise to an ice-cooled solution prepared from 1.22 g (3.5 mmol) of an 80 percent solution of 3,5-dichloro-4-(1,1,2,2-tetrafluoroethoxy)aniline in DMF, 0.42 g (4.2 mmol) of triethylamine and 40 ml of methylene chloride. The reaction mixture was stirred at room temperature overnight and then poured into a dilute aqueous HCl solution. The organic layer was separated, washed with a saturated aqueous NaHCO3 solution, dried over MgSO4 and evaporated to dryness. The residual material, a gum, was purified by preparative scale liquid chromatography, eluting with an 86:14 hexane:acetone mixture. After removal of the solvent, there was left 1.02 g (47 percent of theoretical) of the above-named product as a light yellow glassy material. The structure of the product was confirmed by its IR and NMR spectrum (NMR Spectrum: (d6-DMSO); 8.55 (br, m, 1H); 8.45 (br, 1H); 7.9 (s, 2H); 6.6–7.2 (m, 5H); 4.9 (q, 1H); 1.6 (d, 3H). (Compound 2)

|  | % C | % H | % N |
|---|---|---|---|
| Analysis: | | | |
| Calc. for $C_{23}H_{14}Cl_3F_7N_2O_4$: | 44.43 | 2.27 | 4.51 |
| Found: | 44.77 | 2.22 | 4.97 |

EXAMPLE III 2-(4-((6-Fluoro-2-quinolinyl)oxy)phenoxy)-N-(4-(trifluoromethoxy)phenyl)propanamide

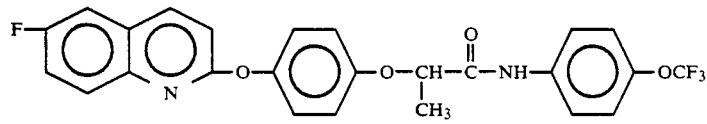

A solution of 5 mmol of 2-(4-((6-fluoro-2-quinolinyl)oxy)phenoxy)propionyl chloride in 5 milliliters (ml) of methylene chloride was slowly added to an ice-cooled solution comprising 1.17 grams (g) (5.5 mmol) of 4-(trifluoromethoxy)aniline hydrochloride and 1.21 g (12 mmol) of triethylamine in 40 ml of methylene chloride. The reaction mixture was stirred at 0° C. for 30 minutes then at room temperature for 3 hours. The mixture was poured into a dilute aqueous HCl solution. The organic layer was separated, washed with water, then washed with a saturated aqueous NaHCO3 solution, dried over MgSO4 and evaporated to dryness. The residual solid was taken up in methylene chloride and filtered through a short column of silica gel, eluting with additional methylene chloride. After removal of the solvent, the residue was recrystallized from methylcyclohexane to give 1.0 g (41 percent of theoretical) of the above-named product as colorless crystals. The product melted at 134°–136° C. and its structure was confirmed by its infrared (IR) and its nuclear magnetic resonance (NMR) spectrum. (Compound 3)

|           | % C   | % H  | % N  |
|-----------|-------|------|------|
| Analysis: |       |      |      |
| Calc. for C$_{25}$H$_{18}$F$_4$N$_2$O$_4$: | 61.73 | 3.73 | 5.76 |
| Found: | 61.62 | 3.43 | 5.71 |

EXAMPLE IV 2-(4-((6-Fluoro-2-quinoxalinyl)oxy)phenoxy)-N-(4-(1,1,2,2-tetrafluoroethoxy)phenyl)propanamide

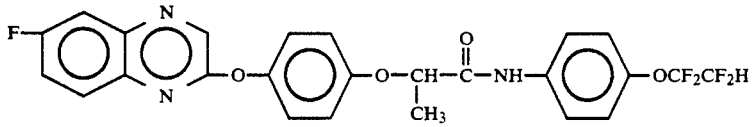

Step A:

A mixture of 1.50 g (4.57 mmol) of 2-(4-((6-fluoro-2-quinoxalinyl)oxy)phenoxy)propanoic acid and 20 ml of thionyl chloride was warmed at reflux for 45 minutes. The excess thionyl chloride was removed by vacuum distillation and the resulting acid chloride product was used without further purification.

Step B:

A solution of the acid chloride prepared in Step A in 15 ml of acetonitrile was added to a mixture prepared from 1.12 g (4.57 mmol) of 4-(1,1,2,2-tetrafluoroethoxy)aniline hydrochloride and 1.16 g (11.43 mmol) of triethylamine in 10 ml of acetonitrile. The reaction mixture was warmed at reflux for 2.5 hours and then poured into ice water. The resulting precipitate was collected by filtration, washed with water and dried to give 1.90 g (80 percent of theoretical) of the above-named product. The product was a tan solid and melted at 155°–157° C. and its structure was confirmed by its IR and NMR spectrum. (Compound 4)

|           | % C   | % H  | % N  |
|-----------|-------|------|------|
| Analysis: |       |      |      |
| Calc. for C$_{25}$H$_{18}$R$_5$N$_3$O$_4$: | 57.81 | 3.49 | 8.09 |
| Found: | 57.82 | 3.27 | 8.20 |

EXAMPLE V 2-(4-((3-Chloro-5-(trifluoromethyl)-2-pyridinyl)oxy)-phenoxy)-N-(4-(1,1,2,2-tetrafluoroethoxy)phenyl)-propanamide

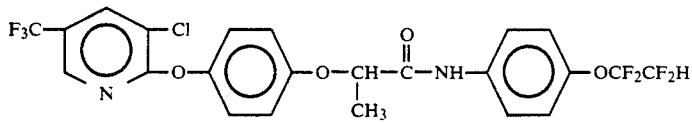

Step A:

A mixture of 2.00 g (5.53 mmol) of 2-(4-((3-chloro-5-(trifluoromethyl)-2-pyridinyl)oxy)phenoxy)propanoic acid and 20 ml of thionyl chloride was warmed at reflux for 45 minutes. The excess thionyl chloride was removed by vacuum distillation and the resulting acid chloride was used without further purification.

Step B:

A solution of the acid chloride prepared in Step A in 20 ml of acetonitrile was added to a mixture prepared from 1.36 g (5.53 mmol) of 4-(1,1,2,2-tetrafluoroethoxy)aniline hydrochloride and 1.40 g (13.8 mmol) of triethylamine in 10 ml of acetonitrile. The reaction mixture was warmed at reflux for 2.5 hours and then poured into ice water. The resulting solid precipitate was collected by filtration and dried. The solid was then recrystallized from methylcyclohexane to give 2.50 g (82 percent of theoretical) of the above-named product as a tan solid melting at 114°–116° C. The structure of the product was confirmed by its IR and NMR spectrum. (Compound 5). The carbon, hydrogen and nitrogen contents were determined to be as follows:

|           | % C   | % H  | % N  |
|-----------|-------|------|------|
| Analysis: |       |      |      |
| Calc. for C$_{23}$H$_{16}$ClF$_7$N$_2$O$_4$: | 49.97 | 2.92 | 5.07 |
| Found: | 50.35 | 2.55 | 5.40 |

EXAMPLE VI 2-(4-((6-Chloro-2-quinoxalinyl)oxy)phenoxy)-N-(4-(trifluoromethoxy)phenyl)propanamide

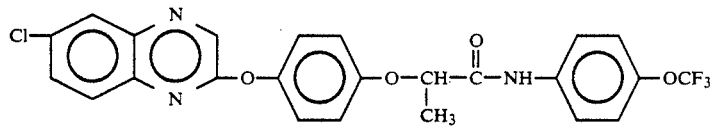

A solution of 6.5 mmol of 2-(4-((6-chloro-2-quinoxalinyl)oxy)phenoxy)propionyl chloride in 10 ml of methylene chloride was added dropwise to an ice-cooled solution of 1.53 g (7.2 mmol) of 4-(trifluoromethoxy)aniline hydrochloride and 1.58 g (15.6 mmol) of triethylamine in 40 ml of methylene chloride. The reaction mixture was stirred at room temperature overnight and then poured into a dilute aqueous HCl solution. The organic layer was separated, washed with a saturated aqueous NaHCO$_3$ solution, dried over MgSO$_4$ and evaporated to dryness. The residual solid was recrystal-

EXAMPLE VIII 2-(4-((6-Fluoro-2-quinoxalinyl)oxy)phenoxy)-N-(4-(trifluoromethoxy)phenyl)propanamide

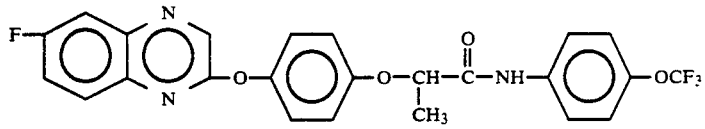

(Compound 6)

|  | % C | % H | % N |
|---|---|---|---|
| Analysis: |  |  |  |
| Calc. for $C_{24}H_{17}ClF_3N_3O_4$: | 57.20 | 3.40 | 8.34 |
| Found: | 56.95 | 3.42 | 8.46 |

A solution of 6.1 mmol of 2-(4-((6-fluoro-2-quinoxalinyl)oxy)phenoxy)propionyl chloride in 15 ml of methylene chloride was added dropwise to an ice-cooled solution of 1.43 g (6.7 mmol) of 4-(trifluoromethoxy)aniline hydrochloride and 1.54 g (15 mmol) of triethylamine in 40 ml of methylene chloride. The reaction mixture was stirred at room temperature for 3 hours and then poured into a dilute aqueous HCl solution. The organic layer was separated, washed with a saturated $NaHCO_3$ solution, dried over $MgSO_4$ and evaporated to dryness. The residual solid was taken up in boiling methanol, treated with charcoal and filtered through celite. The filtrate was allowed to cool to give 1.14 g (38 percent of theoretical) of the above-named product as colorless crystals which melted at 140.5°-142° C. The structure of the compound was confirmed by its IR and NMR spectrum. (Compound 8)

|  | % C | % H | % N |
|---|---|---|---|
| Analysis: |  |  |  |
| Calc. for $C_{24}H_{17}F_4N_3O_4$: | 59.14 | 3.52 | 8.62 |
| Found: | 59.05 | 3.55 | 8.71 |

EXAMPLE VII 2-(4-((6-Chloro-2-quinoxalinyl)oxy)phenoxy)-N-(4-(1,1,2,2-tetrafluoroethoxy)phenyl)propanamide

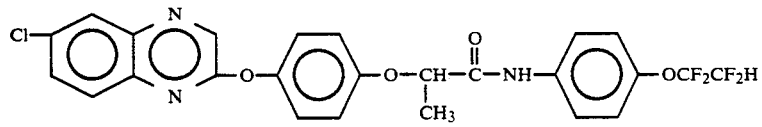

Step A:

A mixture of 1.50 g (4.35 mmol) of 2-(4-((6chloro-2-quinoxalinyl)oxy)phenoxy)propanoic acid and 20 ml of thionyl chloride was warmed at reflux for 45 minutes. The excess thionyl chloride was removed by distillation and the resulting acid chloride was used without further purification.

Step B:

In solution of the acid chloride prepared in Step A in 20 ml of acetonitrile was added to a mixture prepared from 1.07 g (4.35 mmol) of 4-(1,1,2,2-tetrafluoroethoxy)aniline hydrochloride, 1.10 g (10.9 mmol) of triethylamine and 10 ml of acetonitrile. The reaction mixture was stirred at reflux for 3 hours and then poured into ice water. The resulting precipitate was filtered, washed with water and dried to give 2.1 g (90 percent of theoretical) of the desired product as a tan solid melting at 146°-148° C. The structure of the compound was confirmed by its IR and NMR spectrum. (Compound 7). The carbon, hydrogen and nitrogen contents were determined to be as follows:

|  | % C | % H | % N |
|---|---|---|---|
| Analysis: |  |  |  |
| Calc. for $C_{25}H_{18}ClF_4N_3O_4$: | 56.04 | 3.39 | 7.84 |
| Found: | 55.88 | 3.32 | 7.88 |

EXAMPLE IX 2-(4-((6-Chloro-2-quinolinyl)oxy)phenoxy)-N-(4-(trifluoromethoxy)phenyl)propanamide

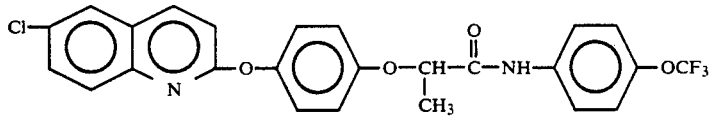

A mixture of 1.5 g (4.36 mmol) of 2-(4-((6-chloro-2-quinolinyl)oxy)phenoxy)propanoic acid and 15 ml of thionyl chloride was warmed at reflux for a period of 45 minutes. The resulting solution was evaporated to dryness under vacuum, 5 ml of toluene added to the residue and the solution again evaporated to dryness. The residual acid chloride was used immediately.

A solution of the acid chloride prepared above in 15 ml of acetonitrile was added to a mixture prepared from 0.93 g (4.36 mmol) of 4-(trifluoromethoxy)aniline hydrochloride, 1.10 g (10.9 mmol) of triethylamine and 10 ml of acetonitrile. The mixture was warmed at reflux for 2.5 hours, cooled and poured into ice water. The resulting precipitate was collected by filtration, dried and then recrystallized from methylcyclohexane to give 1.8 g (82 percent of theoretical) of the above-named product as a tan solid, m.p. 133°—135° C. (Compound 9)

Analysis:

| | % C | % H | % N |
|---|---|---|---|

-continued

| | % C | % H | % N |
|---|---|---|---|
| Calc. for $C_{25}H_{18}ClF_3N_2O_4$: | 59.71 | 3.61 | 5.57 |
| Found: | 59.65 | 3.69 | 5.62 |

By following the hereinabove procedures of Example IX employing the appropriate starting acid chloride and aniline reactants, the following compounds in Table 6 are prepared.

TABLE 6

$$Ar-O-\underset{}{\bigcirc}-O-\underset{CH_3}{\overset{}{CH}}-\overset{O}{\underset{}{C}}-NH-\underset{(J)_p}{\bigcirc}-OC_nX^2_{2n\pm1}$$

| Compound No. | Ar | $-OC_nX^2_{2n\pm1}$ | $J_p$ | M.P. °C. | Molecular Formula and Elemental Analysis |
|---|---|---|---|---|---|
| 10 | Cl-[6-chloroquinoxalinyl] | $-OCH_2CH{:}CHCl$ | $-H$ | 154–156 | $C_{26}H_{21}Cl_2N_3O_4$<br>Calc. 61.19 4.15 8.23<br>Found: 61.30 4.30 8.43 |
| 11 | Cl-[6-chloroquinoxalinyl] | $-OCH_2CFHCF_2$ | $-H$ | 141–143 | $C_{26}H_{18}ClF_6N_3O_4$<br>Calc. 53.30 3.10 7.17<br>Found: 53.17 3.22 7.07 |
| 12 | Cl-[6-chloroquinoxalinyl] | $-OCH(CH_2F)_2$ | $-H$ | 148–150 | $C_{26}H_{22}ClF_2N_3O_4$<br>Calc. 60.77 4.32 8.18<br>Found: 60.55 4.34 8.16 |
| 13 | Cl-[6-chloroquinoxalinyl] | $-OCH_2CH_2F$ | $-H$ | 176–178 | $C_{25}H_{21}ClFN_3O_4$<br>Calc. 62.31 4.39 8.72<br>Found: 62.19 4.44 8.50 |
| 14 | Cl-[6-chloroquinoxalinyl] | $-OCF_2CF_2Br$ | $-H$ | 145–148 | $C_{25}H_{17}BrClF_4N_3O_4$<br>Calc. 48.84 2.79 6.84<br>Found: 48.99 2.95 7.32 |
| 15 | Cl-[6-chloroquinoxalinyl] | $-OCF{:}CFH$ | $-H$ | 139–141 | $C_{25}H_{18}ClF_2N_3O_4$<br>Calc. 60.31 3.64 8.44<br>Found: 59.52 3.69 8.28 |
| 16 | Cl-[6-chloroquinoxalinyl] | $-OCF_2CF_2H$ | 2-$CH_3$ | 161–162 | $C_{26}H_{20}F_4N_3O_4$<br>Calc. 56.78 3.67 7.64<br>Found: 56.67 3.69 7.68 |
| 17 | Cl-[6-chloroquinoxalinyl] | $-OCF_2CCl_2H$ | $-H$ | 141–144 | $C_{25}H_{18}Cl_3F_2N_3O_4$<br>Calc. 52.79 3.19 7.39<br>Found: 52.95 3.28 7.64 |
| | | | | | $C_{25}H_{18}F_3N_3O_4$ |

TABLE 6-continued

Structure: Ar—O—⟨C6H4⟩—O—CH(CH3)—C(=O)—NH—⟨C6H3(J)p⟩—OC$_n$X$^2_{2n\pm1}$

| Compound No. | Ar | —OC$_n$X$^2_{2n\pm1}$ | J$_p$ | M.P. °C. | Molecular Formula and Elemental Analysis | | | |
|---|---|---|---|---|---|---|---|---|
| | | | | | | % C | % H | % N |
| 18 | Cl-quinoxalinyl | —OCF$_2$CFClH | —H | 134–137 | Calc. | 54.37 | 3.29 | 7.61 |
| | | | | | Found: | 54.64 | 3.41 | 7.67 |
| 19 | Cl-quinoxalinyl | —OCH$_2$CF$_3$ | —H | 151–152.5 | C$_{25}$H$_{19}$ClF$_3$N$_3$O$_4$ | | | |
| | | | | | Calc. | 57.98 | 3.70 | 8.11 |
| | | | | | Found: | 58.19 | 3.89 | 8.21 |
| 20 | Cl-quinoxalinyl | —OCF:CFCl | —H | 149–151 | C$_{25}$H$_{17}$Cl$_2$F$_2$N$_3$O$_4$ | | | |
| | | | | | Calc. | 56.41 | 3.22 | 7.89 |
| | | | | | Found: | 56.20 | 3.27 | 7.97 |
| 21 | Cl-quinoxalinyl | —OCH$_2$CF$_2$CF$_3$ | —H | 148–150 | C$_{26}$H$_{19}$ClF$_5$N$_3$O$_4$ | | | |
| | | | | | Calc. | 54.99 | 3.37 | 7.40 |
| | | | | | Found: | 55.22 | 3.39 | 7.46 |
| 22 | Cl-quinoxalinyl | —OCH$_2$CF$_2$CF$_2$H | —H | 165–166 | C$_{26}$H$_{20}$ClF$_4$N$_3$O$_4$ | | | |
| | | | | | Calc. | 56.79 | 3.67 | 7.64 |
| | | | | | Found: | 57.21 | 3.85 | 7.70 |
| 23 | F-quinoxalinyl | —OCH$_2$CF$_3$ | —H | 159–161 | C$_{25}$H$_{19}$F$_4$N$_3$O$_4$ | | | |
| | | | | | Calc. | 59.88 | 3.82 | 8.38 |
| | | | | | Found: | 60.37 | 4.08 | 8.46 |
| 24 | Cl-quinoxalinyl | —OCF$_2$CFBrH | —H | 133–135 | C$_{25}$H$_{18}$ClBrF$_3$N$_3$O$_4$ | | | |
| | | | | | Calc. | 50.32 | 3.04 | 7.04 |
| | | | | | Found: | 50.46 | 3.07 | 7.17 |
| 25 | Cl-quinoxalinyl | —OCF$_2$CH$_2$Cl | —H | 137–139 | C$_{25}$H$_{19}$Cl$_2$F$_2$N$_3$O$_4$ | | | |
| | | | | | Calc. | 56.20 | 3.58 | 7.86 |
| | | | | | Found: | 56.65 | 3.71 | 8.04 |
| 26 | Cl-quinoxalinyl | —OCF$_2$CBr$_2$H | —H | 172–174 | C$_{25}$H$_{18}$Br$_2$ClF$_2$N$_3$O$_4$ | | | |
| | | | | | Calc. | 45.66 | 2.76 | 6.39 |
| | | | | | Found: | 45.97 | 2.83 | 6.67 |
| 27 | Cl-quinoxalinyl | —OCH(CH$_3$)CF$_3$ | —H | 155–157 | C$_{26}$H$_{21}$ClF$_3$N$_3$O$_4$ | | | |
| | | | | | Calc. | 58.71 | 3.98 | 7.90 |
| | | | | | Found: | 58.65 | 4.13 | 8.00 |
| | | | | | C$_{27}$H$_{19}$ClF$_7$N$_3$O$_4$ | | | |

TABLE 6-continued

Ar—O—⟨○⟩—O—CH(CH₃)—C(=O)—NH—⟨○⟩(J)ₚ—OCₙX²₂ₙ±₁

| Compound No. | Ar | $-OC_nX^2_{2n\pm1}$ | $J_p$ | M.P. °C. | Molecular Formula and Elemental Analysis | | |
|---|---|---|---|---|---|---|---|
| | | | | | | % C | % H | % N |
| 28 | 6-Cl-quinoxalin-2-yl | $-OCH_2(CF_2)_2CF_3$ | —H | 150–152 | Calc. | 52.49 | 3.10 | 6.80 |
| | | | | | Found: | 52.61 | 3.23 | 7.03 |
| 29 | 6-Cl-quinoxalin-2-yl | $-OCH_2CH_2CH_2F$ | —H | 152–154 | $C_{26}H_{23}ClFN_3O_4$ Calc. | 62.97 | 4.68 | 8.47 |
| | | | | | Found: | 63.05 | 4.82 | 8.74 |
| 30 | 6-Cl-quinoxalin-2-yl | $-OCH_2CF_3$ | 3-F | 152–153.5 | $C_{25}H_{18}ClF_4N_3O_4$ Calc. | 56.03 | 3.38 | 7.84 |
| | | | | | Found: | 55.65 | 3.37 | 7.96 |
| 31 | 3-F, 5-CF₃-pyridin-2-yl | $-OCF_3$ | —H | 106–107 | $C_{22}H_{15}F_7N_2O_4$ Calc. | 52.39 | 3.00 | 5.56 |
| | | | | | Found: | 52.38 | 3.03 | 5.67 |
| 31A | 6-Cl-quinoxalin-2-yl | $-OCF_2H$ | —H | 144–148 | $C_{24}H_{18}ClF_2N_3O_4$ Calc. | 59.33 | 3.73 | 8.65 |
| | | | | | Found: | 59.51 | 3.85 | 8.92 |

EXAMPLE X 2-(4-((6-Bromo-2-quinoxalinyl)oxy)phenoxy)-N-(4-(trifluoromethoxy)phenyl)propanamide

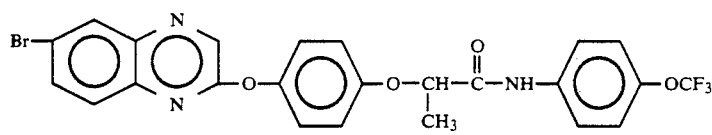

(Compound 32)

A solution of 5.5 mmol of 2-(4-((6-bromo-2-quinoxalinyl)oxy)phenoxy)propanoyl chloride (previously prepared from the corresponding acid and thionyl chloride) in 15 ml of methylene chloride was added dropwise to an ice-cooled mixture prepared from 1.29 g (6.1 mmol) of 4-(trifluoromethoxy)aniline hydrochloride, 1.39 g (14 mmol) of triethylamine and 40 ml of methylene chloride. The resulting mixture was stirred overnight and then poured into dilute aqueous HCl. The aqueous phase was separated and extracted with CH₂Cl₂. The combined organic layers were washed twice with saturated aqueous sodium bicarbonate, dried over MgSO₄ and evaporated to dryness. The residue was recrystallized from toluene/methylcyclohexane to give 2.27 g (75 percent of theoretical) of the above-named product as colorless crystals, m.p. 149°–151° C.

| | % C | % H | % N |
|---|---|---|---|
| Analysis: | | | |
| Calc. for $C_{24}H_{17}BrF_3N_3O_4$: | 52.57 | 3.13 | 7.66 |
| Found: | 52.23 | 3.29 | 7.66 |

By following the hereinabove procedure of Example X employing the appropriate starting material, the following compound is prepared.

| Compound No. | Compound | M.P. °C. |
|---|---|---|

-continued

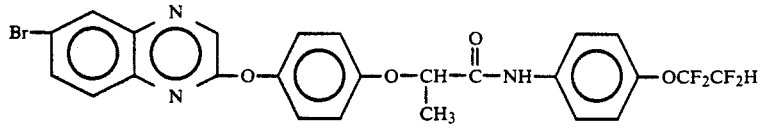

33  156-158

| | | % C | % H | % N |
|---|---|---|---|---|
| Analysis: | Calc. for C$_{25}$H$_{18}$BrF$_4$N$_3$O$_4$: | 51.74 | 3.13 | 7.24 |
| | Found: | 51.52 | 3.24 | 7.29 |

EXAMPLE XI 2-(4-((6-Fluoro-2-quinoxalinyl)oxy)phenoxy)-N-(4-(trifluoromethoxy)phenyl)propanthioamide

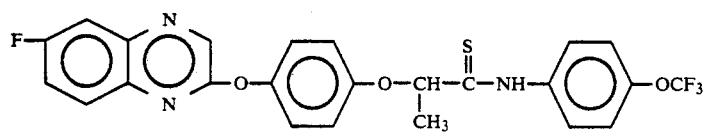

A mixture of 2.0 g (4.1 mmol) of 2-(4-((6-fluoro-2-quinoxalinyl)oxy)phenoxy)-N-(4-(trifluoromethoxy)phenyl)propanamide and 40 ml of dry THF in a 100 ml flask was placed in a water-filled ultrasonic bath. Phosphorous pentasulfide (0.22 g) was added and the mixture sonicated while maintaining the reaction temperature below 40° C. by occasional addition of ice to the water bath. Additional P$_2$S$_5$ (1.76 g) was added in portions at 20 minute intervals over the next hour. Sonication was continued for an additional 2 hours and the mixture then filtered and the solid washed well with methylene chloride. The combined filtrates were treated with charcoal, filtered and evaporated to dryness. The residue was purified first by chromatography over silica gel, eluting with CH$_2$Cl$_2$, and then by preparative scale HPLC, eluting with 85:15 hexane: acetone. This left 1.1 g (53 percent of theoretical) of the above-named product as a yellow glassy solid. (Compound 34)

| | | % C | % H | % N | % S |
|---|---|---|---|---|---|
| Analysis: | | | | | |
| | Calc. for C$_{24}$H$_{17}$F$_4$N$_3$O$_3$S: | 57.25 | 3.40 | 8.35 | 6.37 |
| | Found: | 57.25 | 3.58 | 8.09 | 6.33 |

By following the hereinabove procedure of Example XI employing the appropriate starting amide, the following compound is prepared.

| Compound No. | Compound | M.P. °C. |
|---|---|---|
| 35 | 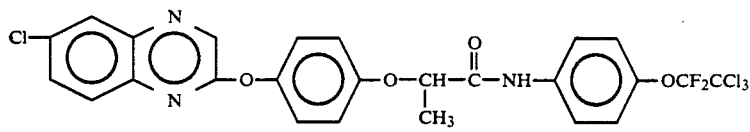 | 106-108 |

| | | % C | % H | % N | % S |
|---|---|---|---|---|---|
| Analysis: | Calc. for C$_{25}$H$_{19}$ClF$_3$N$_3$O$_3$S: | 56.23 | 3.59 | 7.87 | 6.01 |
| | Found: | 55.19 | 3.77 | 7.71 | 6.03 |

EXAMPLE XII 2-(4((6-Chloro-2-quinoxalinyl)oxy)phenoxy)-N-(4-(1,1-difluoro-2,2,2-trichloroethoxy)phenyl)propanamide A solution of 4.35 mmol of 2-(4-((6-chloro-2-quinoxalinyl)oxy)phenoxy)propanoyl chloride (previously prepared from 1.5 g of the corresponding acid) in 15 ml of acetonitrile was added to a mixture prepared from 1.20 g (4.35 mmol) of 4-(1,1-difluoro-2,2,2-trichloroethoxy)aniline, 0.66 g (6.5 mmol) of triethylamine and 10 ml of acetonitrile. The mixture was warmed at reflux for a period of 2.5 hours and then poured over ice and aqueous NaOH added. The resulting precipitate was filtered and dried and then recrystallized from methylcyclohexane. This left 2.2 g (84 percent of theoretical) of the above-named product as a brown solid, m.p. 139°-141° C. (Compound 36)

| | % C | % H | % N |
|---|---|---|---|
| Analysis: | | | |
| Calc. for $C_{25}H_{17}Cl_4F_2N_3O_4$: | 49.78 | 2.84 | 6.97 |
| Found: | 49.99 | 2.95 | 7.37 |

EXAMPLE XIII 2-(4-((5-Chloro-3-fluoro-2-pyridinyl)oxy)phenoxy)-N-(4-(trifluoromethoxy)phenyl)propanamide

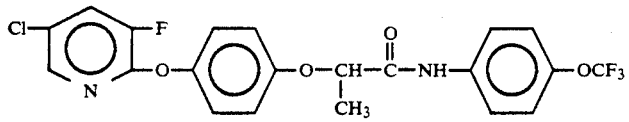

A solution of 4.8 mmol of 2-(4-((5-chloro-3-fluoro-2-pyridinyl)oxy)phenoxy)propanoyl chloride (previously prepared from the corresponding acid) in 15 ml of methylene chloride was added, under $N_2$, to an ice-cooled mixture of 1.03 g (4.8 mmol) of 4-(trifluoromethoxy)aniline hydrochloride, 0.95 g (12 mmol) of pyridine and 25 ml of methylene chloride. The resulting mixture was stirred at ambient temperature overnight and then poured into dilute aqueous HCl. The aqueous layer was separated and extracted with $CH_2Cl_2$. The combined organic layers were washed twice with saturated aqueous sodium bicarbonate, treated with charcoal and $MgSO_4$ and filtered. The filtrates were evaporated to dryness and the residue recrystallized from methylcyclohexane to give 0.34 g of the above-named product as colorless crystals, m.p. 92°-93.5° C. (Compound 37)

| | % C | % H | % N |
|---|---|---|---|
| Analysis: | | | |
| Calc. for $C_{21}H_{15}ClF_4N_2O_4$: | 53.57 | 3.21 | 5.95 |
| Found: | 53.31 | 3.26 | 5.75 |

EXAMPLE XIV 2-(4-((5-Trifluoromethyl-2-pyridinyl)oxy)phenoxy)-N-(4-(trifluoromethoxy)phenyl)propanamide

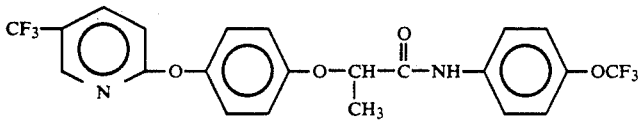

A mixture of 1.26 g (5.0 mmol) of 4-((5-trifluoromethyl)-2-pyridinyl)oxy)phenol, 1.40 g (4.5 mmol) of 2-bromo-N-(4-(trifluoromethoxy)phenyl)propanamide, 0.75 g (5.4 mmol) of powdered, anhydrous potassium carbonate and 40 ml of acetonitrile was warmed at reflux for a period of 3 hours. The mixture was cooled, poured into water and extracted with two portions of methylene chloride. The combined organic layers were washed with 2 percent aqueous NaOH, dried over $MgSO_4$ and evaporated to dryness. The residue was recrystallized from methylcyclohexane to give 1.74 g (79 percent of theoretical of the above-named product as colorless crystals, m.p. 96.5°-98° C. (Compound 38)

| | % C | % H | % N |
|---|---|---|---|
| Analysis: | | | |
| Calc. for $C_{22}H_{16}F_6N_2O_4$: | 54.33 | 3.32 | 5.76 |
| Found: | 54.25 | 3.38 | 5.72 |

EXAMPLE XV 2-(4-((5-Iodo-2-pyrimidinyl)oxy)phenoxy)-N-(4-(trifluoromethoxy)phenyl)propanamide

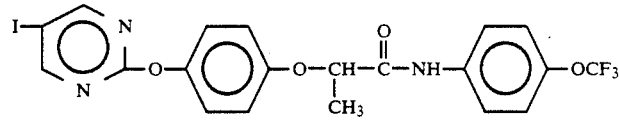

A mixture of 0.44 g (1.8 mmol) of 2-chloro-5-iodopyrimidine, 0.68 g (2 mmol) of 2-(4-hydroxyphenoxy)-N-(4-(trifluoromethoxy)phenyl)propanamide, 0.30 g (2.2 mmol) of powdered, anhydrous potassium carbonate and 25 ml of DMSO was warmed, under $N_2$ at 100° C. for a period of two hours. The resulting mixture was poured into water and extracted with two portions of ether. The combined organic layers were washed with two portions of 5 percent aqueous NaOH, dried over $MgSO_4$ and evaporated to dryness. The residue was recrystallized from methylcyclohexane to give 0.54 g (55 percent of theoretical) of the above-named product as colorless crystals, m.p. 106°-107° C. (Compound 39)

| | % C | % H | % N |
|---|---|---|---|
| Analysis: | | | |
| Calc. for $C_{20}H_{15}F_3IN_3O_4$: | 44.05 | 2.77 | 7.71 |
| Found: | 44.19 | 2.80 | 7.51 |

EXAMPLE XVI 2-(4-((6-Chloro-2-quinoxalinyl)oxy)phenoxy)-N-(4-(1,1,2-trifluoroethoxy)phenyl)propanamide

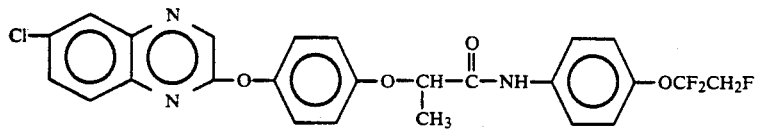

A solution of 5.8 mmol of 2-(4-((6-chloro-2-quinoxalinyl)oxy)phenoxy)propanoyl chloride (previously prepared from 2.0 g, 5.8 mmol, of the corresponding acid) in 15 ml of acetonitrile was added to a mixture of 1.32 g (5.8 mmol) of 4-(1,1,2-trifluoroethoxy)benzeneamine hydrochloride (contaminated with approximately 20 percent of 4-(1,2-difluoroethenyloxy)benzeneamine), 1.47 g (14.5 mmol) of triethylamine and 15 ml of acetonitrile. The mixture was stirred at reflux for 2.5 hours, poured over ice and made basic with dilute aqueous sodium hydroxide. The resulting precipitate was filtered and dried (2.9 g, 97 percent of theoretical) and then recrystallized from methylcyclohexane. This gave the desired product (contaminated with approximately 20 percent of 2-(4-((6-chloro-2-quinoxalinyl)oxy)phenoxy)-N-(4-(1,2-difluoroethenyloxy)phenyl)propanamide) as a solid, m.p. 137°-140° C. (Compound 40)

|  | % C | % H | % N |
|---|---|---|---|
| Analysis: |  |  |  |
| Calc. for $C_{25}H_{19}ClF_3N_3O_4$: | 57.98 | 3.70 | 8.11 |
| Found: | 58.81 | 3.76 | 8.47 |

EXAMPLE XVII 2-(4-((6-Fluoro-2-quinoxalinyl)oxy)phenoxy)-N-methyl-N-(4-(trifluoromethoxy)phenyl)propanamide

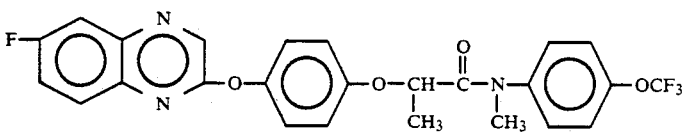

A mixture of 0.23 g (5.7 mmol) of a 60 percent NaH-/oil dispersion and 10 ml of hexane was stirred under $N_2$ for 10 minutes. The hexane was decanted off, replaced with 20 ml of DMF and a solution of 2.0 g (4.1 mmol) of 2-(4-((6-fluoro-2-quinoxalinyl)oxy)phenoxy)-N-(4-(trifluoromethoxy)phenyl)propanamide in 20 ml of DMF was added dropwise over a period of 30 minutes. The mixture was stirred at ambient temperature for 1.5 hours when a solution of 1.45 g (10 mmol) of methyl iodide in 10 ml of DMF was slowly added. The mixture was stirred at ambient temperature for 2 days and then quenched by cautious addition of a few drops of acetic acid and then water. The mixture was poured into water, extracted with three portions of ether and the combined organic layers dried over $MgSO_4$ and evaporated to dryness. The residue was taken up in hot methylcyclohexane, treated with charcoal and filtered and then allowed to cool to give 1.03 g (50 percent) of the above-named product as colorless crystals, m.p. 137°-139° C. (Compound 41)

|  | % C | % H | % N |
|---|---|---|---|
| Analysis: |  |  |  |
| Calc. for $C_{25}H_{19}F_4N_3O_4$: | 59.88 | 3.82 | 8.38 |
| Found: | 60.02 | 4.01 | 8.13 |

PREPARATION OF STARTING MATERIALS

The carboxylic acids, acid halides and esters employed herein as starting materials and which correspond to the formula

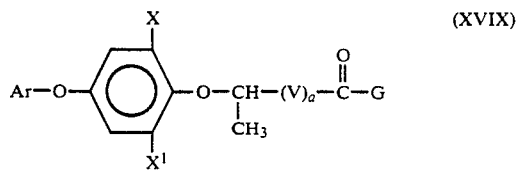

(XVIX)

wherein G represents —OH, —$X^3$ or OR and Ar, X, Xl, $(V)_a$ and R are as hereinbefore set forth are for the most part known compounds and various compounds corresponding to Formula XVIX and their preparation can be found in the known art including Canadian Patent 1,179,350; European Patent Applications 23,785; 47,972; 50,019; British Patent 2,042,539; Japanese Kokai 55-111467; 55-120565 and 55-154936; U.S. Pat. Nos. 4,236,912; 4,325,729 and 4,444,584; and U.S. patent application Ser. No. 550,328, filed Nov. 10, 1983. In addition, compounds of Formula XVIX not specifically taught can be prepared by procedures analogous to those of the above references.

The aromatic/heterocyclic halides employed as starting materials and which correspond to the formula

Ar—$X^4$ (X)

wherein Ar and $X^4$ are as hereinbefore defined, are all known and/or commercially produced compounds and for the most part are taught in the above-listed applications and/or patents which teach preparing compounds of Formula XVIX.

The aniline compounds employed as starting materials and which correspond to the formula

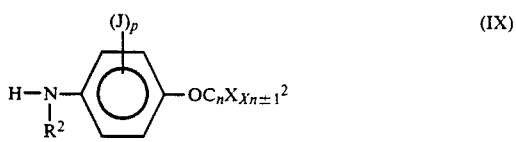

(IX)

wherein $R^2$, $X^2$, J, n and p are as hereinbefore defined and $-OC_nX^2_{2n\pm 1}$ haloalkoxy radical are for the most part known compounds as shown and/or taught in U.S. Pat. Nos. 3,387,037; 3,954,442; 4,170,657; 4,276,310 4,468,405; J. Org. Chem. 29, pages 1-11, (1964); C.A. 51:15518C and C.A. 76:72216s. Many of the compounds are well known and those compounds not specifically known can be prepared by the processes used to prepare the known compounds employing the appropriate starting materials.

Many of the compounds corresponding to Formula IX wherein $-OC_nX^2_{2n\pm 1}$ is a haloalkenyloxy radical can be prepared by subjecting a compound corresponding to Formula IX wherein $-OC_nX^2_{2n\pm 1}$ is a haloalkoxy to conventional mild dehydrohalogenation conditions.

In one method for preparing the aniline compounds wherein R is hydrogen, a two step procedure is employed. In the first step, an appropriate halonitrobenzene which corresponds to the formula

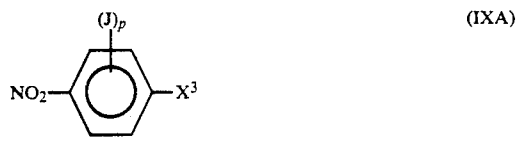

(IXA)

is reacted with an appropriate alkanol corresponding to the formula

$HO-C_nX^2_{2n\pm 1}$ (IXB)

In carrying out this reaction, excess alkanol in a dry solvent such as DMSO, acetonitrile, acetone or DMF slowly is mixed at a temperature of from about 0° C. to about 30° C. with a cooled mixture of sodium hydride and one of the above solvents. To this mixture is slowly added at a temperature of from about 0° C. to about 30° C., the halonitrobenzene in one of the above solvents. The reaction mixture is agitated and the reaction is complete in from about 30 minutes to about 4 hours. The mixture is poured into water and the solid product recovered by filtration, or extraction, dried and further purified, if required.

In the second step, the above produced nitro product is reduced to the aniline, by convention methods such as those taught in Wagner et al., cited supra, pages 654-657. In one preferred procedure, the product is mixed with stannous chloride in a solvent such as ethanol and heated to reflux for from about 30 minutes to about 2 hours. The reaction mixture is poured over ice and made basic. The precipitate which forms is removed by filtration or extraction and dissolved in a solvent such as ether. Hydrogen chloride gas is bubbled in said solvent solution to cause the aniline product to precipitate as the hydrochloride salt which is recovered and can be employed as such.

In another procedure for preparing the anilines of Formula IX, equimolar amounts of an appropriate phenol of the formula

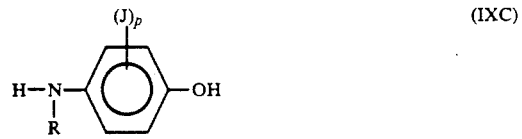

(IXC)

is reacted with an appropriate halo compound of the formulae

$C_nX^2_{2n}$ or $C_nX^2_{2n+2}$ (IXD)

in the presence of a solvent and a strong base. In carrying out this reaction, the phenol reactant of Formula IXC is slowly added to a mixture of a strong base such as sodium hydride, sodium hydroxide, potassium carbonate or potassium hydroxide in a solvent such as one of those listed directly hereinabove. To this mixture is added the halo compound reactant of Formula IXD. The mixture is stirred at from about 20° to about 90° C., until the reaction is complete, usually within from about 1 hour to several days. The mixture is poured into water neutralized with base and the precipitate recovered by filtration or extraction. The aniline product is recovered employing the above outlined work-up procedure for recovering an aniline product.

EXAMPLE XVIII

P-(1,3-Difluoro-2-propoxy)nitrobenzene

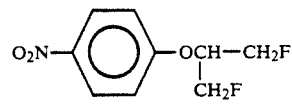

Step A 1.18 g (49.3 mmol) of sodium hydride and 30 ml of dry DMF were combined and cooled to 0° C. 4.3 g (44.8 mmol) of 1,3-difluoro-2-propanol in 10 ml dry DMF was added over a period of 25 minutes at 0°-5° C., and the mixture was stirred for 15 minutes. 5.06 g (35.8 mmol) of p-fluoronitrobenzene in 10 ml of dry DMF was added over a period of 30 minutes at 0°-5° C. The mixture was stirred at 0° C. for 1 hour, then poured into water. The yellow solid was collected by filtration, dried and recrystallized from hexane/toluene to give 4.0 g (51 percent of theoretical) of the above-named product as a pale yellow solid (m.p. 48°-50° C.).

|  | % C | % H | % N |
|---|---|---|---|
| Analysis: |  |  |  |
| Calc. for $C_9H_9F_2NO_3$: | 49.78 | 4.18 | 6.45 |
| Found: | 49.80 | 4.25 | 6.52 |

EXAMPLE XIX 4-(1,3-Difluoro-2-propoxy)benzeneamine

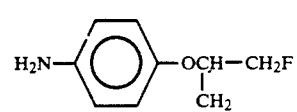

Step B 3.4 g (15.7 mmol) of p-(1,3-difluoro-2-propoxy)nitrobenzene, 17.7 g (78.5 mmol) of $SnCl_2\cdot 2H_2O$ and 35 ml of absolute ethanol were heated together at reflux for 1 hour. The reaction mixture was poured over ice, made basic with 50 percent aqueous NaOH and extracted three times into ether. The combined ether extracts were washed two times with water, dried over $MgSO_4$ and filtered. Hydrogen chloride gas was bubbled into the ether solution causing the above-named aniline to precipitate as the hydrochloride salt. The product was collected as a tan solid by filtration (80 percent of theoretical) and decomposed (d) at 240° C.

| | % C | % H | % N |
|---|---|---|---|
| Analysis: | | | |
| Calc. for $C_9H_{11}F_2NO.HCl$: | 48.33 | 5.41 | 6.26 |
| Found: | 48.42 | 5.41 | 6.33 |

By following the hereinabove procedures of Example XVIII employing the appropriate starting alkanols the following nitro benzenes are prepared in Step 1. Following the reduction procedure of Example XIX, the corresponding anilines are prepared. The compounds are set forth below in Table 7.

TABLE 7

| Compound (a) | Procedure Step | M.P. °C. | | Elemental Analysis | | |
|---|---|---|---|---|---|---|
| | | | | % C | % H | % N |
| 4-(2-fluoroethoxy)nitrobenzene | A | 69–71 | expected: | 51.90 | 4.36 | 7.57 |
| | | | found: | 51.72 | 4.50 | 7.53 |
| 4-(2-fluoroethoxy)benzeneamine | B | d 220–224 | expected: | 50.14 | 5.79 | 7.31 |
| | | | found: | 50.11 | 5.77 | 7.44 |
| 4-(3-fluoro-1-propoxy)nitrobenzene | A | oil | expected: | 54.27 | 5.06 | 7.03 |
| | | | found: | 54.70 | 5.09 | 7.12 |
| 4-(3-fluoro-1-propoxy)benzeneamine | B | 156–160 | expected: | 52.56 | 6.37 | 6.81 |
| | | | found: | 52.75 | 6.39 | 7.00 |
| 4-(2,2,3,3,4,4,4-heptafluoro-1-butoxy)nitrobenzene | A | 50–51 | expected: | 37.40 | 1.88 | 4.36 |
| | | | found: | 37.27 | 1.90 | 4.53 |
| 4-(2,2,3,3,4,4,4-heptafluoro-1-butoxy)benzeneamine | B | d 208–213 | expected: | 36.66 | 2.77 | 4.28 |
| | | | found: | 36.81 | 2.90 | 4.55 |
| 4-(1,1,1-trifluoro-2-propoxy)-nitrobenzene | A | oil | expected: | 45.97 | 3.43 | 5.96 |
| | | | found: | 46.46 | 3.57 | 6.07 |
| 4-(1,1,1-trifluoro-2-propoxy)-benzeneamine | B | 265–270 sub. | expected: | 44.74 | 4.59 | 5.80 |
| | | | found: | 44.53 | 4.61 | 5.88 |
| 4-(2,2,3,3,3-pentafluoro-1-propoxy)-nitrobenzene | A | 56–58 | expected: | 39.87 | 2.23 | 5.17 |
| | | | found: | 39.53 | 2.25 | 5.24 |
| 4-(2,2,3,3,3-pentafluoro-1-propoxy)-benzeneamine | B | d > 200 | expected: | 38.94 | 3.27 | 5.05 |
| | | | found: | 39.51 | 3.36 | 5.13 |
| 4-(2,2,3,3-tetrafluoro-1-propoxy)-nitrobenzene | A | 61–63 | expected: | 42.70 | 2.79 | 5.53 |
| | | | found: | 42.57 | 2.83 | 5.59 |
| 4-(2,2,3,3-tetrafluoro-1-propoxy)-benzeneamine | B | d > 230 | expected: | 41.64 | 3.88 | 5.39 |
| | | | found: | 41.85 | 3.96 | 5.62 | a = all benzamines are made as the hydrochloride salt.
d = decomposition temperature
sub. = sublimation temperature

EXAMPLE XX 4-(1,1-Difluoro-2,2,2-trichloroethoxy)benzeneamine

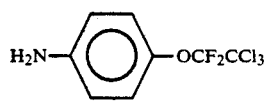

2.0 g (18.3 mmol) of p-aminophenol was added over a period of 10 minutes to a mixture of 0.48 g (20.1 mmol) of sodium hydride in 20 ml of dry DMSO. The mixture was stirred for 20 minutes. 3.73 g (18.3 mmol) of 1,1-difluoro-tetrachloroethane was added causing an exotherm to 47° C. The mixture was stirred at 60° C. for 2 hours, then poured into ice water. The brown solid was collected by filtration, dried, dissolved in ether and then HCl gas was bubbled into the solution causing the above-named aniline to precipitate as the hydrochloride salt. The white solid (4.4 g, 87 percent of theoretical d 250° C.) was collected by filtration.

| | % C | % H | % N |
|---|---|---|---|
| Analysis: | | | |
| Calc. for $C_8H_6Cl_3F_2NO.HCl$: | 30.70 | 2.25 | 4.48 |
| Found: | 30.79 | 2.24 | 4.96 |

EXAMPLE XXI 4-(2-Chloro-1,1-difluoroethoxy)benzeneamine

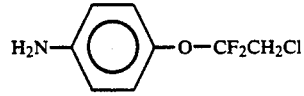

2.5 g (22.9 mmol) of p-aminophenol, 3.09 g (22.9 mmol) of 1,2-dichloro-1,1-difluoroethane, 5.48 g (39.6 mmol) of $K_2CO_3$ and 40 ml of dry acetonitrile were stirred together at room temperature for 5 days. The mixture was poured into water and extracted two times into ether. The combined ether extracts were washed with water, dried over $MgSO_4$ and filtered: HCl gas was bubbled into the ether solution causing the above-named aniline to precipitate as the hydrochloride salt, which was collected by filtration and recrystallized twice from $CH_3CN$ to give 0.9 g (16 percent of theoretical d 245°–250° C.) of a white solid.

| | % C | % H | % N |
|---|---|---|---|
| Analysis: | | | |
| Calc. for $C_8H_8ClF_2NO.HCl$: | 39.37 | 3.70 | 5.74 |
| Found: | 39.45 | 3.63 | 5.86 |

EXAMPLE XXII 4-(1,1,2-Trifluoroethoxy)benzeneamine

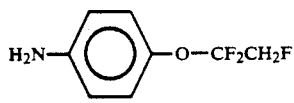

Gaseous trifluoroethylene was bubbled into a mixture of 7.0 g (64.1 mmol) of p-aminophenol, 0.7 g (12.8 mmol) of powdered KOH, and 70 ml dry DMF at 90° C. for 1¼ hours. The mixture was poured into ice water and extracted 2 times with ether. The combined ether layers were washed with diluted aqueous NaOH, washed with water, dried over MgSO₄ and filtered. HCl was bubbled into the ether solution. The resulting gray solid was collected by filtration to give 3.6 g (25 percent of theoretical) of the above-named aniline as the HCl salt along with a 20 percent impurity of 4-(1,2-difluoroethenyloxy)benzene-amine.

EXAMPLE XXIII 4-(1,1-Difluoro-2,2-dibromoethoxy)benzeneamine

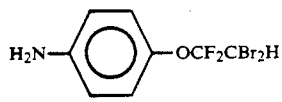

10.7 g (48.1 mmol) of 1,1-dibromo-2,2-difluoroethylene in 15 ml DMF was added over a period of 10 minutes to a mixture of 5.0 g (45.8 mmol) p-aminophenol, 0.5 g (9.2 mmol) powdered KOH and 40 ml DMF, causing an exotherm to 44° C. The mixture was stirred at 50° C. for 30 minutes, then poured over ice and extracted two times into ether. The combined ether layers were washed with dilute aqueous NaOH, washed with water, dried over MgSO₄, decolorized with charcoal and filtered HCl gas was bubbled into the ether solution causing the above-named aniline to precipitate as the hydrochloride salt. The tan solid (9.1 g, 54 percent of theoretical, d 265°-270° C.) was collected by filtration.

|  | % C | % H | % N |
|---|---|---|---|
| Analysis: |  |  |  |
| Calc. for $C_8H_7Br_2F_2NO \cdot HCl$: | 26.15 | 2.19 | 3.81 |
| Found: | 26.18 | 2.20 | 3.89 |

EXAMPLE XXIV 4-(1,2-Difluoroethenyloxy)benzeneamine

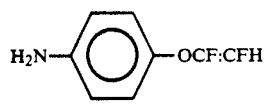

4.05 g (61.2 mmol) of zinc dust was added to a mixture of 5.0 g (16.3 mmol) of p-(2-bromo-1,1,2-trifluoroethoxy)benzeneamine hydrochloride 5 ml of 6N⁵HCl and 45 ml of glacial acetic acid. The mixture was stirred at room temperature for 3½ hours, then poured into ice, made basic with 50 percent aqueous NaOH and extracted two times into ether. The combined ether layers were washed with dilute aqueous NaOH, washed with water, dried over MgSO₄ and filtered. HCl gas was bubbled into the solution. The resulting white solid was collected by filtration to give 3.0 g (88 percent of theoretical) of the above-named aniline as the hydrochloride salt along with a 10 percent impurity of 4-(1,1,2-trifluoroethoxy)benzeneamine.

EXAMPLE XXV 4-(2-Chloro-1,3-difluoroethenyloxy)benzeneamine

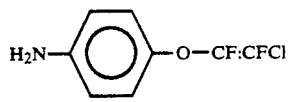

4.3 g (32 mmol) of 1,2-dichloro-1,2-difluoroethylene was added to a mixture of 3.5 g (32 mmol) of p-aminophenol, 2.16 g (38.5 mmol) of powdered KOH and 40 ml of DMF, causing an exotherm to 52° C. The mixture was heated at 50°-60° C. for 1 hour, then poured over ice water and extracted into ether. The ether extract was washed with aqueous base, washed with water, dried over MgSO₄ and the solvent was removed by rotary evaporation to give a brown oil. The extract was then purified by HPLC eluting with 70:30 hexane:acetone to give a yellow oil which was dissolved in ether. HCl gas was bubbled into the ether solution causing the above-named aniline to precipitate as the hydrochloride salt. The beige solid (4.8 g 62 percent of theoretical, d >200° C) was collected by filtration.

|  | % C | % H | % N |
|---|---|---|---|
| Analysis for $C_8H_6ClF_2NO \cdot HCl$: | 39.70 | 2.92 | 5.79 |
| Found: | 39.65 | 2.91 | 5.84 |

The substituted amides employed as starting materials and which correspond to the formula

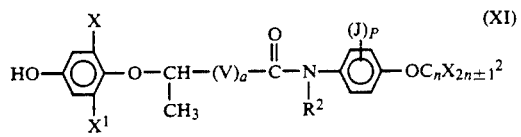

wherein X, $X^1$, $X^2$, $(V)_a$, $R^2$, J, n and p are as hereinbefore defined, can be prepared by the reaction of substantially equimolar amounts of an appropriate ester corresponding to the formula

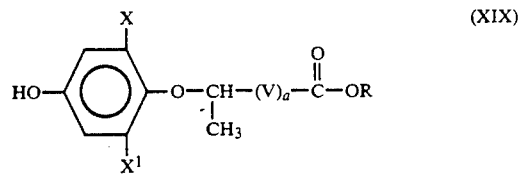

wherein X, $X^1$, $(V)_a$ and R are as hereinabove defined (taught in the references for preparing compounds of Formula XIII) with an appropriate aniline compound of Formula IX, in an inert, non-acidic polar solvent. In carrying out this reaction, the reactants and the solvent are mixed together and heated at a temperature of from about 50° C. up to the refluxing temperature of the mixture. After the completion of the reaction, the product is recovered after the removal of the solvent and any excess amine; in most cases, evaporation procedures are sufficient.

In an alternative procedure for preparing the amide of Formula (XI), substantially equimolar amounts of an appropriate hydroquinone which contains a protecting group (W) and which corresponds to the formula

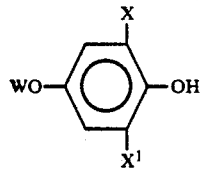
(XXI)

wherein X and $X^1$ as hereinbefore defined and W represents a protecting group are reacted with a substituted amide corresponding to the formula

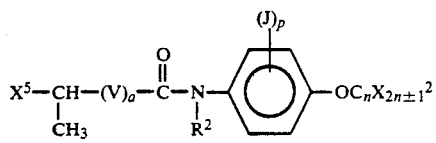
(XXII)

wherein $X^2$, $(V)_a$, $R^2$, J, n and p are hereinbefore defined and $X^5$ is —Br or —Cl.

Protecting groups and their use in reactions involving hydroquinone compounds are well known to those skilled in the art. Such usage is taught in "Protective Groups in Organic Synthesis" by T. W. Greene; Chapter 3 *Protection For Phenols and Catechols;* John Wiley & Sons, N.Y., N.Y.; (1981), which is being incorporated herein by reference thereto. The specific protecting group employed is not critical, any of the conventionally employed protecting groups can be employed herein as long as this group is not reactive with the amide. Representative groups include —CH₃, —CH₂OCH₃, —CH₂OCH₂CH₂OCH₃ and the like.

In carrying out this reaction, the protected hydroquinone and the amide are mixed together in an inert dipolar, aprotic solvent such as, for example, acetonitrile, acetone, methyl ethyl ketone, DMF or DMSO. In addition, a strong base such as an anhydrous alkali metal carbonate, hydroxide or hydride is present to deprotonate the hydroquinone. The reaction is conducted at a temperature of from about 25° C. up to the reflux temperature of the mixture. At the completion of this reaction, the product is usually recovered employing conventional steps including extraction, water and alkali washing and distillation.

The above product is then deprotected employing a variety of techniques depending upon the nature of the protecting group. The above cited Greene reference describes such techniques. As one example, the above product where W is —CH₂OCH₃ is mixed with an alcoholic solvent and a catalytic amount of a strong acid and refluxed for up to 24 hours to convert the product to the desired hydroxy compound. Representative acids include p-toluenesulfonic acid, and the like. The product is thereafter recovered employing conventional procedures of solvent evaporation, solvent extraction and the like.

The substituted amide of Formula XXII can be prepared by the reaction of equimolar amounts of an appropriate acid chloride corresponding to the formula

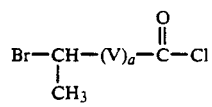
(XXIIa)

with an appropriate benzeneamine of Formula IX in the presence of a solvent and a hydrogen halide absorber. This reaction can be carried out employing the procedures and conditions employed for the reaction of compounds VIII and IX.

EXAMPLE XXVI

2-Bromo-N-(4-(trifluoromethoxy)phenyl)propanamide

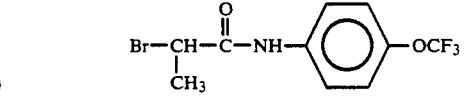

A solution of 4.02 g (23.4 mmol) of 2-bromopropionyl chloride in 10 ml of methylene chloride was added to an ice-cooled solution of 5.0 g (23.4 mmol) of 4-(trifluoromethoxy)aniline hydrochloride, 4.65 g (59 mmol) of pyridine and 30 ml of methylene chloride. The mixture was stirred at ambient temperature for a period of 2.5 hours and then washed with two portions of dilute aqueous HCl and two portions of saturated aqueous sodium bicarbonate, dried over MgSO₄, treated with charcoal, filtered and the filtrates evaporated to dryness. The residue was recrystallized from methylcyclohexane to give 5.43 g 74 percent of theoretical) of the above-named product as colorless crystals, m.p. 111°-112° C.

|  | % C | % H | % C |
|---|---|---|---|
| Analysis: |  |  |  |
| Calc. for $C_{10}H_9BrF_3NO_2$: | 38.48 | 2.91 | 4.49 |
| Found: | 39.06 | 2.96 | 4.49 |

EXAMPLE XXVII 2-(4-(Methoxymethoxy)phenoxy)-N-(4-(trifluoromethoxy)phenyl)propanamide

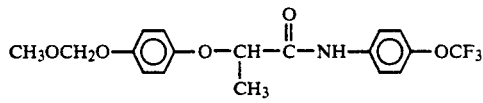

A mixture of 2.91 g (9.3 mmol) of 2-bromo-N-(4-(trifluoromethoxy)phenyl)propanamide, 1.58 g (10 mmol) of 4-(methoxymethoxy)phenol, 1.52 g (11 mmol) of powdered, anhydrous potassium carbonate and 35 ml of acetonitrile was warmed, under N₂, at reflux for a period of 5.5 hours and then stirred at room temperature overnight. The resulting mixture was poured into water and extracted with two portions of ether. The combined organic layers were washed twice with 5 percent aqueous NaOH, treated with charcoal and MgSO₄, filtered and the filtrates evaporated to dryness. The residue was recrystallized from hexane to leave 1.77 g (49 percent of theoretical) of the above-named product as a colorless solid, m.p. 115°-116° C. The product is identified on the basis of IR and NMR analyses.

EXAMPLE XXVIII 2-(4-Hydroxyphenoxy)-N-(4-(trifluoromethoxy)-phenyl)propanamide

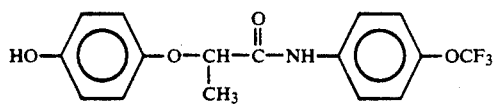

A solution of 1.70 g (4.4 mmol) of 2-(4-methoxymethoxy)phenoxy)-N-(4-trifluoromethoxy)phenyl)-propanamide, 0.1 g of p-toluenesulfonic acid monohydrate and 20 ml of methanol was warmed at reflux for a period of 3.5 hours. The solution was cooled, neutralized with a few drops of saturated aqueous NaHCO and evaporated to dryness. The residue was partitioned between ether and water and the aqueous layer separated and again extracted with ether. The combined organic layers were dried over $MgSO_4$ and evaporated to dryness. The resulting solid was recrystallized from hexane containing a small amount of acetone to give 1.10 g (73 percent of theoretical) of the above-named product as colorless crystals, m.p. 74.5°–75° C. The product is identified on the basis of IR and NMR analyses.

|  | % C | % H | % N |
|---|---|---|---|
| Analysis: |  |  |  |
| Calc. for $C_{16}H_{14}F_3NO_4$: | 56.31 | 4.13 | 4.11 |
| Found: | 56.06 | 4.03 | 3.77 |

In a variation of the above procedure, the amide of Formula XXII can be prepared directly from the unprotected hydroquinone by the slow addition of the amide of Formula XXI to a mixture containing one of the above solvents, strong base and an excess of the hydroquinone.

EXAMPLE XXIX 4-(Methoxymethoxy)phenol

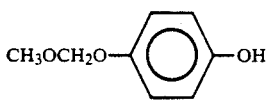

A mixture of 55.0 g (0.5 mol) of hydroquinone, 500 milligrams (mg) of p-toluenesulfonic acid monohydrate, 200 ml of dimethoxymethane and 1000 ml of methylene chloride was warmed to a vigorous reflux. The distillate was passed through a soxhlet extractor which had been charged with approximately 300 g of 4Å molecular sieves. After 18 hours an additional 500 mg of p-toluenesulfonic acid monohydrate was added and refluxing continued for an additional 24 hours. The reaction mixture was then cooled and 20 ml of triethylamine was added and the mixture filtered. The filtrates were evaporated to near dryness and the residue partitioned between ether and saturated aqueous sodium bicarbonate. The ether layer was extracted twice with portions of 5 percent aqueous sodium hydroxide. The combined aqueous layers were washed with ether and then made acidic with acetic acid. The aqueous mixture was extracted twice with portions of ether and the combined ether layers washed with saturated aqueous sodium bicarbonate, dried over $MgSO_4$ and evaporated to dryness. The residue was distilled in a Kugelrohr apparatus at 120° C. and 0.07 mm Hg to give 37.1 g (48 percent of theoretical) of a reddish oil which was identified by NMR analysis as 4-(methoxymethoxy)phenol contaminated with a small amount of hydroquinone. The residual hydroquinone was removed by dissolving the oil in methylene chloride, washing the solution with water and then, after removal of the solvent, distilling the residue as before. This left 30.4 g of pure 4-(methoxymethoxy)phenol, as an oil.

The compounds of the present invention have been found to be suitable for use in methods for the pre- and postemergent control of many annual and perennial grassy weeds. In addition, the present compounds are sufficiently tolerant toward most broadleafed and some grass crops, such as, for example, soybeans, cotton, sugar beets, corn, rice and wheat, to allow for the postemergent control of grassy weeds growing among said crops. It is to be noted that not all compounds will have the same effect on all plants. Some compounds will be more active in the control of one weed specie than another and some compounds will be more selective toward one crop specie than another.

For such uses, unmodified active ingredients of the present invention can be employed. However, the present invention also embraces the use of the active compounds in admixture with inert materials, known in the art as an agricultural adjuvants and/or carriers, in solid or liquid form. Thus, for example, an active ingredient can be dispersed on a finely-divided solid and employed therein as a dust or granule. Also, the active ingredients, as liquid concentrates or solid compositions comprising one or more of the active ingredients can be dispersed in water, typically with aid of a wetting agent, and the resulting aqueous dispersion employed as a spray. In other procedures, the active ingredients can be employed as a constituent of organic liquid compositions, oil-in-water and water-in-oil emulsions or water dispersions, with or without the addition of wetting, dispersing, or emulsifying agents. Suitable adjuvants of the foregoing type are well known to those skilled in the art.

The herbicidally effective concentration of the active ingredients in solid or liquid compositions generally is from about 0.0003 to about 95 percent by weight or more. Concentrations from about 0.05 to about 50 percent by weight are often employed. In compositions to be employed as concentrates, the active ingredient can be present in a concentration from about 5 to about 98 weight percent. The active ingredient compositions can also contain other compatible additaments, for example, phytotoxicants, plant growth regulants and other biologically active compounds used in agriculture.

In further embodiments, the compounds of the present invention or compositions containing the same, can be advantageously employed in combination with one or more additional pesticidal compounds. Such additional pesticidal compounds may be insecticides, nematocides, miticides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use or as an additament. The compounds in combination can generally be present in a ratio of from 1 to 100 parts of the compound of the present invention with from 100 to 1 part of the additional compound(s).

The active ingredients of the present invention have been found to possess desirable postemergent activity against grassy weeds such as foxtail, barnyard grass, wild oats, Johnson grass and crabgrass while showing high selectivity to important broadleaf crops such as cotton, sugar beets and soybeans and grassy crops such as wheat, rice and corn. These compounds are also uniquely effective in selectively controlling perennial grassy weeds such as Johnson grass, quackgrass, and bermuda grass in the presence of said crop plants.

The exact amount of the active material to be applied is dependent not only on the specific active ingredient being applied, but also on the particular action desired, the plant species to be controlled and the stage of growth thereof as well as the part of the plant to be contacted with the toxic active ingredient. Thus, all of the active ingredients of the present invention and compositions containing the same may not be equally effective at similar concentrations or against the same plant species.

In preemergent operations a dosage rate of 0.01 to 10 lbs/acre (0.011 to 11.2 kgs/hectare), preferably 0.05 to 2.0 lbs/acre (0.056 to 2.25 kgs/hectare) and most preferably 0.1 to 1 lb/acre (0.11 to 1.12 kgs/hectare) is generally employed.

In postemergent operations a dosage of about 0.01 to about 20 lbs/acre (0.056-22.4 kg/hectare) is generally applicable, although not all compounds are equally effective and some weeds are more difficult to control. Thus, a dosage rate in the range of about 0.05 to about 1.0 lb/acre (0.01-1.12 kg/hectare) is preferred in postemergent control of annual grassy weeds, while about 0.05 to about 5 lbs/acre (0.056-5.6 kg/hectare) is a preferred dosage range for the postemergent control of perennial grassy weeds. In applications to tolerant crops a weed controlling but less than crop damaging amount of from about 0.005 to about 1.0 lb/acre (0.0056 to 1.12 kgs/hectare) is generally employed.

The following examples illustrate the effects of the compounds of this invention.

EXAMPLE XXX

Representative compositions of the present invention were evaluated to determine their effectiveness in preemergent operations.

Aqueous dispersions were prepared by admixing one of the hereinafter set forth compounds, dissolved in a predetermined amount of an inert solvent with a predetermined quantity of water and a predetermined amount of a surfactant to give aqueous dispersions of one of the compounds as the sole toxicant.

Seed beds of sandy soil of good nutrient content into which had been planted seeds of one of the hereinafter set forth plant species were treated by spraying the surface of the bed uniformly with one of the hereinafter set forth compositions. The compositions were sprayed to apply the equivalent of 4 pounds per acre of the composition to the beds. Other beds were treated only with a water-surfactant mixture, containing no active compound to serve as controls. After treatment, the beds were maintained for two weeks under greenhouse conditions conducive for good plant growth. At the end of this period, the beds were examined to determine the amount of kill and control. The specific plant species, test compounds, dosage and the percent preemergent control are set forth below in Table 8.

TABLE 8

| Compound No. Tested | Percent Preemergent Kill and Control of the Following Plant Species ||||||||
|---|---|---|---|---|---|---|---|---|
| | Cotton | Morning Glory | Velvet Leaf | Pigweed | Yellow Foxtail | Crabgrass | Barnyard Grass | Wild Oats |
| 1 | 0 | 0 | 0 | 0 | 100 | 100 | 100 | 100 |
| 6 | 0 | 0 | 0 | 0 | 100 | 100 | 100 | 100 |
| 8 | 0 | 0 | 0 | 0 | 100 | 100 | 100 | 100 |

EXAMPLE XXXI

Representative compositions of the present invention were evaluated to determine their effectiveness in preemergent operations.

Aqueous dispersions were prepared by admixing one of the hereinafter set forth compounds, dissolved in a predetermined amount of an inert solvent with a predetermined quantity of water and a predetermined amount of a surfactant to give aqueous dispersions of one of the compounds as the sole toxicant.

Seed beds of sandy soil of good nutrient content into which had been planted seeds of one of the hereinafter set forth plant species were treated by spraying the surface of the bed uniformly with one of the hereinafter set forth compositions. The compositions were sprayed to apply the equivalent of 1 lb per acre of the composition to the beds. Other beds were treated only with a water-surfactant mixture, containing no active compound to serve as controls. After treatment, the beds were maintained for two weeks under greenhouse conditions conducive for good plant growth. At the end of this period, the beds were examined to determine the amount of kill and control. The specific plant species, test compounds, dosage and the percent preemergent control are set forth below in Table 9.

TABLE 9

| Compound No. Tested | Treating rate in Pounds per Acre | Percent Preemergent Kill and Control of the Following Plant Species ||||||||
|---|---|---|---|---|---|---|---|---|---|
| | | Wheat | Corn | Sugar Beet | Soybean | Cotton | Barnyard Grass | Johnson Grass | Yellow Foxtail |
| 1 | 1 | 100 | 100 | 0 | 0 | 50 | 100 | 100 | 100 |
| 8 | 1 | 100 | 90 | 0 | 0 | 0 | 100 | 50 | 100 |

EXAMPLE XXXII

Representative compositions of the present invention were evaluated to determine their effectiveness in postemergent operations.

Aqueous dispersions were prepared by admixing one of the hereinafter set forth compounds, dissolved in a predetermined amount of an inert solvent with a predetermined quantity of water and a predetermined amount of a surfactant to give aqueous dispersions of one of the compounds as the sole toxicant.

Seeds of various plant species were planted in beds of good agricultural soil and grown in a greenhouse. After the plants had emerged and had grown to a height of from 2-8 inches (depending on the plant species), separate beds of the plants were sprayed to runoff with one of the above-prepared compositions at a treating concentration of 4,000 parts of the active compound per million parts of the ultimate composition (PPM). Other beds of the plants were sprayed with a water-surfactant mixture, containing no active compound, to serve as controls. After treatment, the beds were maintained for two weeks under greenhouse conditions conducive for good plant growth. At the end of this period, the beds were examined to determine the amount of kill and control. The specific plant species, test compounds and the percent postemergent control are set forth below in Table 10.

TABLE 10

| Compound No. Tested | Percent Postemergent Kill and Control of the Following Plant Species | | | | | | | |
|---|---|---|---|---|---|---|---|---|
| | Cotton | Morning Glory | Velvet Leaf | Pigweed | Yellow Foxtail | Crabgrass | Barnyard Grass | Wild Oats |
| 1 | 0 | 0 | 0 | 0 | 100 | 100 | 100 | 100 |
| 6 | 0 | 0 | 0 | 0 | 100 | 100 | 100 | 30 |
| 8 | 0 | 0 | 0 | 0 | 100 | 100 | 100 | 40 |

EXAMPLE XXXIII

Representative compositions of the present invention were evaluated to determine their effectiveness in postemergent operations.

Aqueous dispersions were prepared by admixing one of the hereinafter set forth compounds, dissolved in a predetermined amount of an inert solvent with a predetermined quantity of water and a predetermined amount of a surfactant to give aqueous dispersions of one of the compounds as the sole toxicant.

Various plant species were planted in beds of good agricultural soil and grown in a greenhouse. After the plants had emerged and had grown to a height of from 2-8 inches (depending on the plant species), separate beds of the plants were sprayed to run-off with one of the above-prepared compositions at a treating concentration of 31.25, 62.5 or 125 ppm. Other beds were treated only with a water-surfactant mixture, containing no active compound, to serve as controls. After treatment, the beds were maintained for two weeks under greenhouse conditions conducive for good plant growth. At the end of this period, the beds were examined to determine the amount of kill and control. The specific plant species, test compounds, dosage and the percent postemergent control are set forth below in Table 11.

TABLE 11

| Compound No. Tested | Compound Concentration | Percent Postemergent Kill and Control of the Following Plant Species | | | | | | | | |
|---|---|---|---|---|---|---|---|---|---|---|
| | | Wheat | Corn | Sugar Beets | Cotton | Soybean | Crab-Grass | Yellow Foxtail | Barnyard Grass | Johnson Grass |
| 1 | 62.5 | 0 | 30 | 0 | 0 | 0 | 98 | 0 | 0 | 0 |
| 6 | 125 | 20 | 10 | 0 | 0 | 0 | 100 | 100 | 100 | 100 |
|   | 62.5 | 30 | 10 | 0 | 0 | 0 | 100 | 100 | 100 | 100 |
|   | 31.25 | 90[a] | 10 | 0 | 0 | 0 | 100 | 90 | 30 | 40 |
| 8 | 62.5 | 20 | 50 | 0 | 0 | 0 | 100 | 80 | 100 | 100 |

[a] = unknown anomaly

By substantially following the test procedures of Example XXXII employing the active composition at a treating rate of one of 16, 31.25, 62.5 125, 250 or 500 ppm to determine the postemergent selectivity of various active compounds toward corn, the following results in Table 12 are obtained.

TABLE 12

| Compound No. Tested | Treatment Rate in PPM | Percent Kill and Control of the Following Plant Species[b] | | | | | |
|---|---|---|---|---|---|---|---|
| | | Corn | Barnyard Grass | Johnson Grass | Giant Foxtail | Green Foxtail | Yellow Foxtail |
| 1 | 62.5 | 0 | 100 | 100 | 100 | 100 | 100 |
| 3 | 62.5 | 0 | 95 | 100 | 85 | 95 | 20 |
| 4 | 62.5 | 0 | 85 | 80 | 100 | 100 | 98 |
| 5 | 62.5 | 0 | 100 | 100 | 100 | 95 | 100 |
| 6 | 62.5 | 0 | 100 | 100 | 100 | 100 | 100 |
| 7 | 62.5 | 0 | 100 | 100 | 100 | 100 | 100 |
| 8 | 62.5 | 0 | 100 | 100 | 100 | 100 | 100 |
| 9 | 500.0 | 5 | 100 | 100 | 100 | 100 | 100 |
| 17 | 125.0 | 0 | 70 | 100 | 100 | 100 | 90 |
| 19 | 31.25 | 0 | 50 | 100 | 100 | 100 | 100 |
| 20 | 62.5 | 0 | 100 | 100 | 100 | 100 | 100 |
| 31A | 16.0 | 5 | 100 | 50 | 100 | 100 | 90 |
| 32 | 250.0 | 0 | 20 | 40 | 100 | 90 | 100 |
| 33 | 125.0 | 0 | 100 | 100 | 100 | 90 | 100 |

[b] = Percent kill and control determined about two weeks after treatment.

By substantially following the test procedures of Example XXXII employing the active composition at a treating rate of 16, 31.25, 62.5, 125, 250 or 500 ppm to determine the postemergent selectivity of various active compounds toward corn and giant foxtail, the following results in Table 13 are obtained.

TABLE 13

| Compound No. Tested | Treatment Rate in ppm | Percent Kill and Control of the following plant species[b] | |
|---|---|---|---|
| | | Corn | Giant Foxtail |
| 7 | 31.25 | 0 | 95 |
| 10 | 62.5 | 0 | 100 |
| 11 | 250.0 | 0 | 90 |
| 12 | 62.5 | 0 | 100 |
| 13 | 16.0 | 0 | 90 |
| 21 | 250.0 | 0 | 98 |
| 22 | 62.5 | 0 | 95 |
| 23 | 62.5 | 0 | 100 |
| 24 | 125.0 | 0 | 98 |
| 25 | 62.5 | 0 | 100 |
| 27 | 62.5 | 0 | 98 |
| 29 | 62.5 | 0 | 100 |
| 30 | 125.0 | 0 | 100 |
| 34 | 62.5 | 0 | 90 |
| 40 | 31.25 | 0 | 95 |
| 41 | 500.0 | 0 | 98 |

EXAMPLE XXXIV

Representative compositions of the present invention were evaluated to determine their effectiveness in postemergent operations.

Aqueous dispersions were prepared by admixing one of the hereinafter set forth compounds, dissolved in a predetermined amount of an inert solvent with a predetermined quantity of water and a predetermined amount of a surfactant to give aqueous dispersions of one of the compounds as the sole toxicant.

Various plant species were planted in beds of good agricultural soil and grown in a greenhouse. After the plants had emerged and had grown to a height of from 2-8 inches (depending on the plant species), separate beds of the plants were sprayed to run-off with one of the above-prepared compositions, a treating concentration of 125 ppm. Other beds were treated only with a water-surfactant mixture, containing no active compound, to serve as controls. After treatment, the beds were maintained for two weeks under greenhouse conditions conducive for good plant growth. At the end of this period, the beds were examined to determine the amount of kill and control. The specific plant species, test compounds, dosage and the percent postemergent control are set forth below in Table 14.

TABLE 14

| Compound No. Tested | Treatment Rate in PPM | Percent Postemergent Kill and Control of the Following Plant Species | | | | | | | | |
|---|---|---|---|---|---|---|---|---|---|---|
| | | Corn | Rice | Wheat | Sugar-Beets | Cotton | Soybean | Crab-Grass | Yellow Foxtail | Barnyard Grass | Johnson Grass |
| 4 | 125 | 0 | 0 | 0 | 0 | 0 | 0 | 98 | 60 | 100 | 100 |
| 5 | 125 | 0 | 0 | 0 | 0 | 0 | 0 | 95 | 50 | 100 | 100 |
| 6 | 125 | 0 | 0 | 20 | 0 | 0 | 0 | 100 | 90 | 100 | 100 |
| 7 | 125 | 0 | 0 | 0 | 0 | 0 | 0 | 100 | 98 | 100 | 100 |

What is claimed is:

1. A compound or an optical isomer thereof corresponding to the formula

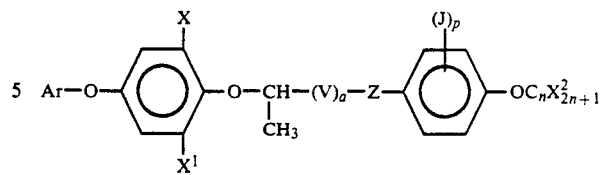

wherein
Ar represents

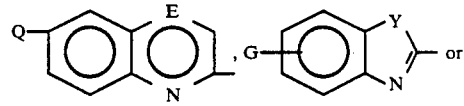

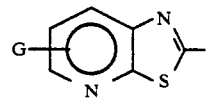

X and $X^1$ each independently represents —H or —F;
each $X^2$ independently represents —H, —Br, —Cl or —F, with the proviso that at least one $X^2$ is other than —H; and that all $X^2$'s cannot be —Br or —Cl;
Y represents oxy9en or sulfur;
Z represents

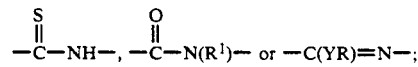

D represents —Br, —Cl, —I, or —CF$_3$;
E represents ≡CH or ≡N;
G represents at the 5 or 6 ring position, —Br, —Cl, —F or —CF$_3$;
R represents $C_1$-$C_4$ alkyl;
$R^1$ represents —H, $C_1$-$C_4$ alkyl, —CH$_2$OH or the agriculturally acceptable salts (—COO$^\ominus$M$^{(+)}$);
J represents —Br, —Cl, —F, —I, —NO, —R, —CN, —OR, —NH$_2$, —NHR, —N(R)$_2$ or —COOR;
T represents —H, —Br, —Cl or —F;
Q represents —Br, —Cl, —F, or —CF ;
V represents —CH$_2$CH$_2$— or —CH=CH—;
a represents an integer of 0 or 1;
n represents an integer of from 1 to 4, inclusive; and
p represents an integer of 0, 1 or 2.

2. A compound as defined in claim 1 which is in the R enantiomeric isomer form.

3. A compound as defined in claim 1 wherein Ar is

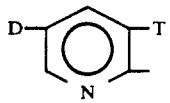

4. A compound as defined in claim 3 wherein D is —Br, —Cl or —CF₃.

5. A compound as defined in claim 4 wherein T is —H, —Cl or —F.

6. A compound as defined in claim 5 wherein T is —Cl.

7. A compound as defined in claim 6 wherein Z is

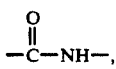

a is 0 and p is 0.

8. A compound as defined in claim 7 wherein n is 1 to 3.

9. A compound as defined in claim 8 wherein n is 1 or 2.

10. The compound as defined in claim 9 which is 2-(4-((3-chloro-5-(trifluoromethyl)-2-pyridinyl)oxy)-phenoxy)-N-(4-(trifluoromethoxy)phenyl)propanamide.

11. The compound as defined in claim 10 which is in the R enantiomeric isomer form.

12. The compound as defined in claim 9 which is 2-(4-((3-chloro-5-(trifluoromethyl)-2-pyridinyl)oxy)-phenoxy)-N-(4-(1,1,2,2-tetrafluoroethoxy)phenyl)-propanamide.

13. The compound as defined in claim 12 which is in the R enantiomeric isomer form.

14. A compound as defined in claim 1 wherein

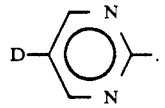

15. A compound as defined in claim 14 wherein D is —I or —CF₃.

16. A compound as defined in claim 1 wherein Ar is

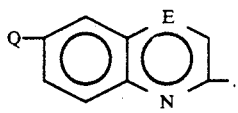

17. A compound as defined in claim 16 wherein E is ≡CH.

18. A compound as defined in claim 16 wherein E is ≡N.

19. A compound as defined in claim 18 wherein Z is

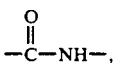

a is 0 and P is 0.

20. A compound as defined in claim 19 wherein n is 1 to 3.

21. A compound as defined in claim 20 wherein Q is —Br.

22. A compound as defined in claim 20 wherein Q is —Cl.

23. The compound as defined in claim 22 which is 2-(4-((6-chloro-2-quinoxalinyl)oxy)phenoxy)-N-(4-(trifluoromethoxy)phenyl)propanamide.

24. The compound as defined in claim 23 which is in the R enantiomeric isomer form.

25. The compound as defined in claim 22 which is 2-(4-((6-chloro-2-quinoxalinyl)oxy)phenoxy)-N-(4-(1,1,2,2-tetrafluoroethoxy)phenyl)propanamide.

26. The compound as defined in claim 25 which is in the R enantiomeric isomer form.

27. The compound as defined in claim 22 which is 2-(4-((6-chloro-2-quinoxalinyl)oxy)phenoxy)-N-(4-(1,2-difluoro-2-chloroethenyloxy)phenyl)propanamide.

28. The compound as defined in claim 27 which is in the R enantiomeric isomer form.

29. The compound as defined in claim 22 which is 2-(4-((6-chloro-2-quinoxalinyl)oxy)phenoxy)-N-(4-(2,2,2-trifluoroethoxy)phenyl)propanamide.

30. The compound as defined in claim 29 which is in the R enantiomeric isomer form.

31. A compound as defined in claim 20 wherein Q is —F.

32. The compound as defined in claim 31 which is 2-(4-((6-fluoro-2-quinoxalinyl)oxy)phenoxy)-N-(4-(trifluoromethoxy)phenyl)propanamide.

33. The compound as defined in claim 32 which is in the R enantiomeric isomer form.

34. The compound as defined in claim 31 which is 2-(4-((6-fluoro-2-quinoxalinyl)oxy)phenoxy)-N-(4-(1,1,2,2-tetrafluoroethoxy)phenyl)propanamide.

35. The compound as defined in claim 34 which is in the R enantiomeric isomer form.

36. The compound as defined in claim 31 which is 2-(4-((6-fluoro-2-quinoxalinyl)oxy)phenoxy)-N-(4-(2,2,2-trifluoroethoxy)phenyl)propanamide.

37. The compound as defined in claim 36 which is the R enantiomeric isomer form.

38. The compound as defined in claim 31 which is 2-(4-((6-fluoro-2-quinoxalinyl)oxy)phenoxy)-N-(4-(3-fluoro-1-propoxy)phenyl)propanamide.

39. The compound as defined in claim 38 which is in the R enantiomeric isomer form.

40. The compound as defined in claim 18 wherein Z is

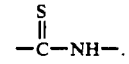

41. The compound as defined in claim 40 which is 2-(4-((6-fluoro-2-quinoxalinyl)oxy)phenoxy)-N-(4-(trifluoromethoxy)phenyl)propanthioamide.

42. The compound as defined in claim 41 which is in the R enantiomeric isomer form.

43. A compound as defined in claim 1 wherein Ar is

44. A compound as defined in claim 43 wherein Y is oxygen.
45. A compound as defined in claim 44 wherein G is —Cl or —F.
46. A compound as defined in claim 43 wherein Y is sulfur.
47. A compound as defined in claim 46 wherein G is —Cl or —F.
48. A compound as defined in claim 1 wherein Ar is
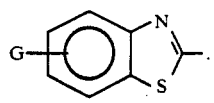
49. A compound as defined in claim 48 wherein G is —Cl or —F.
* * * * *